United States Patent [19]

Bacus

[11] Patent Number: 5,514,554

[45] Date of Patent: May 7, 1996

[54] METHODS AND COMPOSITIONS FOR CANCER THERAPY AND FOR PROGNOSTICATING RESPONSES TO CANCER THERAPY

[75] Inventor: Sarah S. Bacus, Hinsdale, Ill.

[73] Assignee: Becton Dickinson and Company, Franklin Lakes, N.J.

[21] Appl. No.: 50,113

[22] PCT Filed: Aug. 21, 1992

[86] PCT No.: PCT/US92/07117

§ 371 Date: Oct. 7, 1993

§ 102(e) Date: Oct. 7, 1993

Related U.S. Application Data

[63] Continuation-in-part of Ser. No. 767,041, Sep. 27, 1991, abandoned, and a continuation-in-part of Ser. No. 767,042, Sep. 27, 1991, abandoned.

[30] Foreign Application Priority Data

Aug. 22, 1991 [IL] Israel .......................................... 99284

[51] Int. Cl.[6] ........................ G01N 33/574; A61K 39/395

[52] U.S. Cl. .................. 435/7.23; 424/155.1; 424/156.1; 436/501

[58] Field of Search ...................................... 435/7.1, 7.23; 424/2, 85.8, 155.1, 156.1; 436/501

[56] References Cited

U.S. PATENT DOCUMENTS 5,288,477  2/1994  Bacus .......................................... 424/2

Primary Examiner—Mindy Fleisher
Assistant Examiner—Philip W. Carter
Attorney, Agent, or Firm—David W. Highet

[57] ABSTRACT

A method for determining the efficacy of a therapeutic agent, in vitro, for a cancer expressing or overexpressing an oncogene product is described. The method is particularly useful for determining the efficacy of therapeutic agents that have a binding affinity for cancer that express HER-2/neu. N24, N28 and N29 monoclonal antibodies are described which have been identified by this method. One or more of these antibodies can be used as a therapeutic agent in the treatment of breast, stomach, ovarian or salivary cancers.

17 Claims, 7 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( v ) FRAGMENT TYPE: N-terminal (x i) SEQUENCE DESCRIPTION: SEQ ID NO:1:

Glu Val Gln Leu Val Glu Ser Gly Gly Gly Leu Val Gln Pro Lys Gly
1               5                   10                  15

Ser Leu Lys Leu
            20

(2) INFORMATION FOR SEQ ID NO:2:

(i) SEQUENCE CHARACTERISTICS:
      (A) LENGTH: 20 amino acids
      (B) TYPE: amino acid
      (D) TOPOLOGY: linear (i i) MOLECULE TYPE: peptide (v) FRAGMENT TYPE: N-terminal (x i) SEQUENCE DESCRIPTION: SEQ ID NO:2:

Asp Ile Val Met Thr Gln Ser Gln Lys Phe Met Ser Thr Ser Val Val
1               5                   10                  15

Asp Arg Ile Ser
            20

METHODS AND COMPOSITIONS FOR CANCER THERAPY AND FOR PROGNOSTICATING RESPONSES TO CANCER THERAPY

This is a continuation of PCT/US92/07117 which is a continuation-in-part of U.S. applications 07/767,041, filed Sep. 27, 1991, now abandoned, and 07/767,042, filed Sep. 27, 1991, now abandoned.

TECHNICAL FIELD

This invention relates generally to methods for selecting putative anti-cancer agents and for determining the efficacy of such agents useful in the treatment of a cancer characterized by expression of a surface oncogene product. This invention further relates generally to compositions selected by such methods.

BACKGROUND OF THE INVENTION

The transformation of a normal cell into a malignant cell characteristically results, among other things, in the uncontrolled proliferation of the progeny cells, which exhibit immature, undifferentiated morphology, and expression or overexpression of oncogenes not normally expressed by normal, mature cells. It is the goal of cancer therapy to selectively kill or inhibit the uncontrolled growth of such malignant cells, while not adversely effecting normal cells.

Traditional chemotherapeutic agents are highly cytotoxic agents which preferably have greater affinity for malignant cells than normal cells or at least preferentially effect malignant cells based on their high rate of metabolic activity. Where an oncogene product unique to a malignant cell is expressed or overexpressed on its surface membrane, it may be used to target such malignant cells for destruction using chemotherapeutic agents designed to specifically interact with the oncogene product. Extremely precise methods of targeting malignant cells for destruction have become available with the advent of cytotoxic conjugates, consisting of a potent cytotoxin chemically linked to an affinity molecule, such as a monoclonal antibody, having specificity for a unique protein produced by a malignant cell, such as a cell surface antigen. Using immunocytochemical and molecular analyses, it is possible to precisely identify the composition and structure of an oncogenic protein and produce a monoclonal antibody which has the capacity to specifically bind the oncogenic protein, and thus, increase the accuracy of delivering the cytotoxin to the intended target cell.

Besides cytotoxic conjugates, it has been proposed to use monoclonal antibodies which specifically bind to the surface of a cancer cell. Anti-tumor effects of monoclonal antibodies may be achieved through the effector function of the antibody molecule through natural immunological response to the antigen-antibody complex. In this respect, certain monoclonal antibodies have been shown to result in a reduction of tumor size. Undesirably, however, other monoclonal antibodies which specifically bind to such antigens on the surface of the malignant cell have no effect or, worse, actually accelerate the growth of the malignancy, even though such antibodies are specific for the same malignant cell type and the same oncogene product as the antibodies that reduce tumor size. In view of the unpredictability of the effect, if any, of an antibody on malignant cells, it has not been possible to determine, prior to starting therapy, whether one or more selected antibodies would react as anti-tumor agents or provide an accurate prognosis. Heretofore, it has not been possible to determine which antibody preparations, of a selection of monoclonal antibodies (each of which is capable of specifically binding an oncogenic protein) are tumor antagonists, and which are tumor agonists that may undesirably accelerate proliferation of the malignancy. It would be desirable to be able to determine in an in vitro assay method which antibody preparation (or combination of antibodies) having specific affinity for an oncogene product, and how much thereof, would be predicted to inhibit the proliferation of malignant cells and provide a good prognosis for the patient. It would be desirable to provide an in vitro method for prognosticating the efficacy of a proposed therapeutic agent (or combination of agents) and dosage thereof, which method is time-and cost-effective, as well as minimally traumatic to a cancer patient, so that the method may be practically employed in the great variety of cancer cases to be found among different patients.

SUMMARY OF THE INVENTION

We have discovered that in cancers characterized by the presence of malignant cells which express or overexpress one or more membrane-associated, receptor-like oncogene proteins, malignant cells can be induced to terminally differentiate by administering an effective amount of a composition comprising an affinity molecule, such as a monoclonal antibody which is specific for an epitope on the extracellular domain of the oncogene protein, and/or a ligand which is specific for the oncogene protein. In preferred embodiments of the present invention, the malignancy is one that is characterized by the expression or overexpression of at least the HER-2/neu oncogene. Among the cancers which characteristically express or overexpress HER-2/neu are certain breast, stomach, ovarian and salivary gland cancers.

Thus, a method of the present invention entails a method for determining/prognosticating the effectiveness of a therapeutic agent in the treatment of a cancer wherein malignant cells of the cancer express or overexpress an oncogene product, the method comprising the step of: (a) obtaining viable malignant cells which express or overexpress at least one oncogene product and dividing the same into at least first and second portions; (b) treating the first portion comprising viable malignant cells with a sufficient quantity of a composition comprising at least one compound having specific binding affinity for the oncogene product and contacting the second portion with a composition which is devoid of the compound or compounds having specific binding affinity for the oncogene product and incubating the first and second portions in a physiologically acceptable medium for an amount of time sufficient to induce a percentage of the viable malignant cells of said first portion to terminally differentiate; and (c) comparing the percentage of cells in the first portion which exhibit morphological evidence of said terminal differentiation to the percentage of cells in the second portion which exhibit morphological evidence of terminal differentiation, or, alternatively, comparing the average value across the first portion of one or more parameters indicative of terminal differentiation with the average value of the same parameter(s) across the second portion. The viable malignant cells may be obtained as a tissue biopsy, serum sample or other cell containing sample from a patient suffering from a malignancy. In which case a therapeutic agent tailored to the patient may be selected. Alternatively, the malignant cells may be those of an established transformed cell line derived from a malignant tissue, in which case the method of the present invention may be used as a general screening assay for selecting anti-cancer therapeutic agents effective against such malignancy.

In accordance with certain aspects of the present invention, induction of terminal cell differentiation in malignant cells expressing or overexpressing HER-2/neu can be shown by an increased percentage of treated cells which express a mature phenotype. For example, in the case of breast cancer, induction of differentiation in accordance with the present method may be determined by the presence of milk components such as casein and lipid droplets in the treated cells. In accordance with other aspects of the present invention, induction of terminal differentiation in malignant cells expressing or overexpressing HER2/neu can be shown by an increased percentage of cells that express ICAM-1 (designated by the International Workshop on Human Leukocyte Differentiation Antigens as CD54) and/or E-cadherin. (an 80kD protein described in Wheelock et. al., J. Cell. Biochem., 34:187–202 (1987), also known as "CAM 120/80"), and/or an increase in total nuclear area.

It has been found that a sample comprising malignant cells which express or overexpress HER-2/neu, when treated with an affinity molecule which has specific binding affinity for the extracellular domain of the HER-2/neu product, results in terminal cell differentiation and that this differentiation is correlated to translocation of the HER-2/neu product from the surface membrane of a malignant cell to the cytoplasm or perinuclear region of the cell, and to a transient increase in the overall HER-2/neu content of the cell after which translocation the cells ceases to proliferate at rates characteristic of malignant cells. Thus, a monoclonal antibody preparation useful for the treatment of a malignancy characterized by HER-2/neu expression (or overexpression) can be selected based on its ability in a method of the invention to induce in such malignant cells translocation of HER-2/neu protein or the expression of other mature cell phenotypes as discussed below.

Additionally, we have found that, in at least some cancers characterized by the expression or overexpression of a membrane-associated, receptor-like oncogene protein, contacting such malignant cells with a ligand specific for the membrane-associated protein results in the induction of terminal cell differentiation and consequently the appearance in such cells of mature phenotype. In preferred aspects of the invention, the malignant cells express or overexpress the HER-2/neu product and ligands specific for the product are, for example glycoprotein gp30 (Lupu et al., *Science*, 249: 1552–1555 (1990)), and neu differentiation factor (or "NDF" as described in Wen et al., Cell, 69:559–72 (1992)).

Thus, one aspect of the present invention entails methods for selecting anti-cancer therapeutic agents, particularly monoclonal antibodies and ligands, and prognosticating their in vivo response to cancer therapy. A detectable increase in terminal cell differentiation in malignant cells (e.g., from a biopsy treated according to the method of the present invention) represents potential effectiveness of the composition in cancer therapy and provides a prognostic measure of the potential effectiveness of the therapy in vivo.

In another aspect of the present invention, monoclonal antibodies have been selected by application of the above-described method. These antibodies also (1) are specific to the extracellular portion of the human HER2/neu product, (2) are capable of immunoprecipitating a single protein of 185 kD from metabolically labeled HER2 cells, (3) do not react with human epidermal growth factor receptor ("EGFR") or with rat, p 185neu protein, and (4) significantly inhibit the tumorigenic growth of HER2 cells in mice are described. The antibodies N12, N24, and N29 have these properties and were described in Bacus et al., Cancer Res., 52:2580–89 (1992). N28, also described by Bacus et al. has the opposite effect on such cells. N24, N28, N29 and N12 were deposited with the Collection Nationale de Cultures de Microrganismes, Institute Pasteur, 25 Rue du Docteur Roux, Paris, France, under the terms of Rules 28 and 28a of the European Patent Convention as accession numbers 1-1260, 1-1261, 1-1262 and 1-1263 respectively on Aug. 19, 1992. These antibodies, fragments or chimeric/humanized versions thereof, can be used alone (or in combination with each other), and/or linked to toxins to form cytotoxic conjugates any and all of which can be used as therapeutic agents. In addition, these antibodies are useful in the above described prognostic methods.

DESCRIPTION OF PREFERRED EMBODIMENTS

Figure 1:
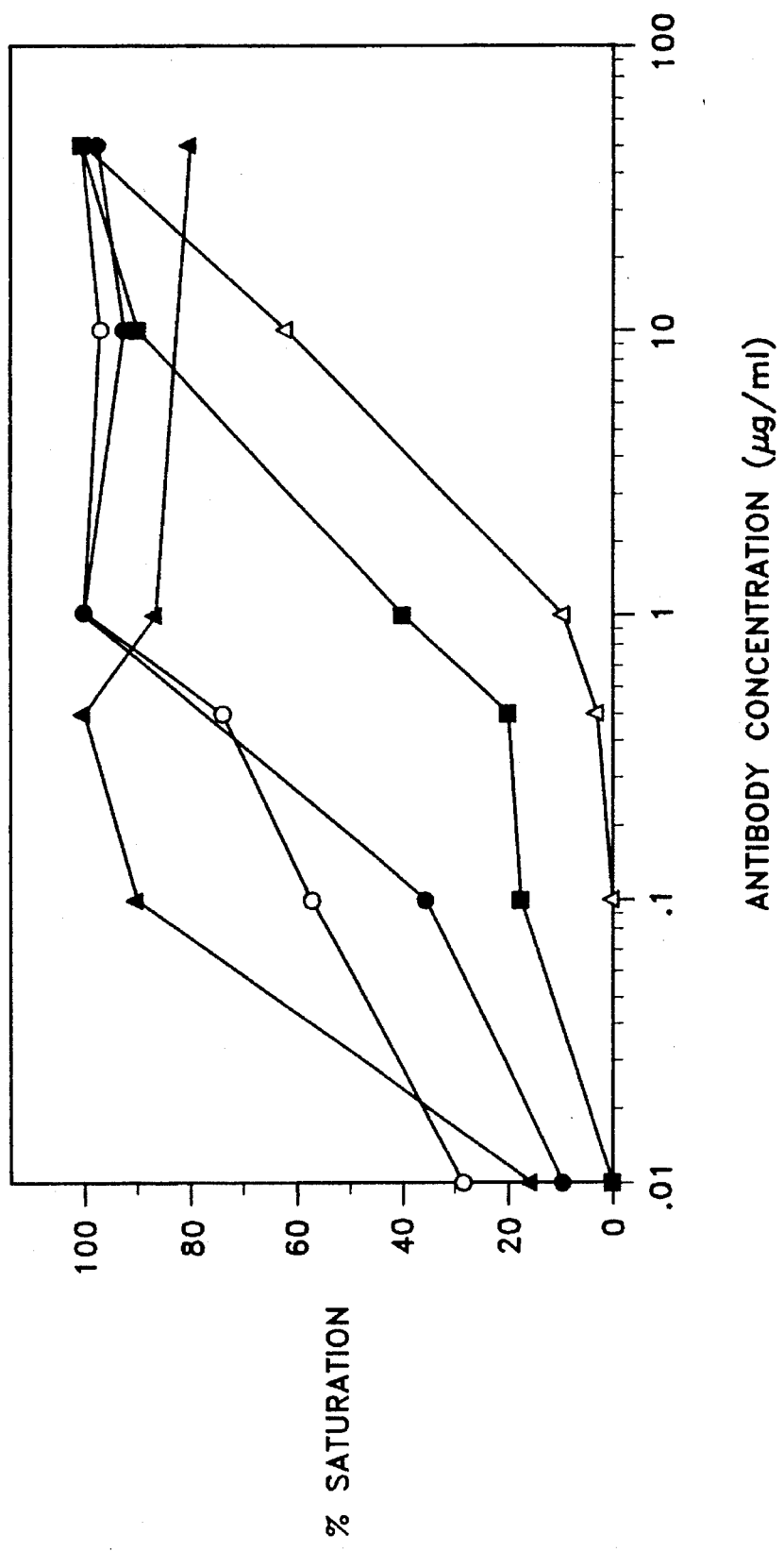
FIG. 1 depicts the binding of anti-HER2/neu monoclonal antibodies to HER2 cells.

In accordance with the present invention, it has been discovered that certain affinity molecules which are capable of specifically binding to the extracellular domain of receptor-like oncogene products, particularly the HER-2/neu oncogene product, have the capacity to induce malignant cells which express or overexpress that product to terminally differentiate and cease unregulated proliferation. The HER-2/neu oncogene is a member of the erbB-2 oncogene family. Administering such affinity molecules to a patient suffering from a malignancy characterized by expression or overexpression of such a product can be used therapeutically, alone or in conjunction with other therapies, to treat patients suffering from such a malignant disease. In accordance with the present invention as it pertains to in vitro assay methods for selecting or determining the efficacy of an affinity molecule which is capable of causing induction of terminal differentiation in a malignant cells of a patient suffering from the malignancy, a cell sample of a cancerous tissue having such malignant cells which express or overexpress an oncogene product is obtained.

Preferably, the cell sample is a biopsy, and is suitably sized so that it may be divided into a plurality of portions for testing with one or more putative agents, at one or more concentrations. While the cell sample may be maintained for up to several days in a suitable maintenance medium, it is preferred to employ a cell sample within about 24 hours or less from the time it is excised.

The cell sample is divided into a first and second portion (each portion then may be further divided into a suitable number of representative aliquots), and the portions placed in individual sterile culture vessels (e.g., separate wells of a microtiter plate). The number of aliquots in a portion that are employed in an assay will be determined by the number of compounds and concentration thereof which are tested. Also, for tissue biopsies it is contemplated, to mince or otherwise disperse the cells so they can be cultured, to provide a suitable number of culture vessels having viable malignant cells grown from the biopsy as primary cultures. In this way, the number of malignant cells obtainable for use in an assay method of the invention may be multiplied. It is preferred to have at least one aliquot of the biopsied tissue (or cells thereof) as a negative control (or second portion) which is not contacted with putative anti-cancer compound(s) so that the percentage of cells exhibiting evidence of terminal cell differentiation in the absence of the putative compounds(s) can be determined.

In accordance with the present invention, a monoclonal antibody or ligand (or a combination of these affinity molecules) can be added to the cultured biopsy after seeding. It is preferred to allow the cells to acclimate to culture conditions for about one day after seeding and then add the putative agent(s) to the respective cultures in amount(s) sufficient to give a predetermined concentration of the agent. Alternatively, a series of tubes of culture media, each of which is supplemented with a predetermined amount of one or more putative agents, can be used to seed the cells directly into the culture vessel.

The aliquots then are incubated for a period of time sufficient to cause induction of terminal cell differentiation in at least a portion of the malignant cells. Generally, a statistically significant percentage of cells (as compared to a negative control) exhibit evidence of terminal cell differentiation within about one to about seven days of incubation in the presence of a compound which has the capacity to induce differentiation. Conventional incubation conditions for human and other mammalian cells are well known in the art. Suitable incubation conditions include an incubation temperature of about 20°–45° C., more preferably about 37° C., and a humidified atmosphere of air supplemented with about 5%–10% $CO_2$. Where incubation times employed in the assay methods of the invention exceed about three or more days, it may be desirable to exchange spent culture medium in the respective vessels for fresh culture medium, preferably supplemented with the same concentration of the putative agent.

While it is preferred to tailor the selection of affinity molecules for use as anti-cancer agents to individual patients by employing a cell sample from such patient in an assay method of the invention, the present invention also includes screening methods for determining the efficacy of affinity molecules such as monoclonal antibodies or ligands having specificity for the HER-2/neu wherein cells of a transformed cell lines are used instead of biopsied tissue, for example. Examples III and IV below describe induction of terminal cell differentiation induced by incubating cells of well-known, readily obtainable transformed cell lines with monoclonal antibody preparations which are specific for a portion of the extracellular domain of the HER-2/neu product.

Monoclonal antibodies which have specific binding affinity for certain regions on the extracellular domain of the HER-2/neu product are one type of affinity molecules which are capable of inducing malignant cells expressing or overexpressing HER-2/neu to undergo terminal cell differentiation. Importantly, it is a necessary, but not sufficient, condition that a monoclonal antibody be specific for an epitope on the extracellular domain of the HER-2/neu product. In other words, not all monoclonal antibodies which are able to specifically bind a region of the extracellular domain of HER-2/neu are able to induce differentiation. Some monoclonal antibodies that meet this first criterion have no effect or, worse, may have an agonistic effect on the proliferation of such malignant cells expressing HER-2/neu, such that their administration in vivo may undesirably promote growth of the malignancy. Also, a monoclonal antibody which is capable of inducing differentiation may have such an effect in one range of concentrations, but have an opposite, agonistic effect, at a different (i.e., higher or lower) concentration. Thus, the present invention provides a method for determining a preferred range of dosages of a therapeutic agent to be used in therapy.

Monoclonal antibodies that are capable of reacting with the HER-2/neu product are known in the art. Methods of making monoclonal antibodies generally also are well known in the art. See, generally, Harlow & Lane, *Antibodies—A Laboratory Manual,* Ch.s 5–6, Cold Spring Harbor (1988). With respect to producing monoclonal antibodies which are specific for the extracellular domain of HER-2/neu, briefly, an animal capable of producing an immune response to the antigen (e.g., HER-2/neu product) is injected with the antigen in a manner which will result in an immune response. The antigen may be HER-2/neu product which has been isolated from malignant cells which produce the protein, or the antigen may be produced by recombinant expression of the HER-2/neu gene (or a portion thereof which encodes at least a portion of the extracellular domain) transformed or transfected as known in the art into in a suitable bacterial, yeast or mammalian host cell for the production of recombinant HER-2/neu product (or protein fragment thereof). Monoclonal antibodies may be produced from mouse lymphocytes by injecting a mouse with a natural or synthetic protein (or part of a protein) or cell membranes derived from whole cells. The immunized animal naturally develops an immune response to the antigen and produces spleen cells which produce antibodies to various epitopes of the antigen, which then are fused with myeloma cells to form hybridomas. Clones with the desired antibody specificity are selected by their ability to (1) bind specifically to the extracellular domain of the HER-2/neu product and (2) induce terminal cell differentiation in viable malignant cells which express or overexpress HER-2/neu. Selected antibody-producing cell lines are expanded by conventional tissue culture techniques and monoclonal antibodies may be routinely purified from the culture medium. Monoclonal antibodies which fulfill criterion (1) and (2) above appear to be able to mimic the action of a ligand for the HER-2/neu product. Chimetic or humanized forms of these antibodies are desirable for in vivo use. Such antibodies can be made in accordance with well known methods one of which is described in U.S. Pat. No. 4,816,397 which is incorporated by reference.

It also has been found, surprisingly, that ligands for the HER-2/neu product are affinity molecules which are capable of inducing malignant cells expressing or overexpressing HER-2/neu to undergo terminal cell differentiation. Examples of such ligands include gp30 and NDF.

After treatment of the portions, the portions are analyzed for indicia of induced terminal differentiation. Phenotypically, induced differentiation is evidenced by maturation markers including inhibition of cell growth, altered cytoplasmic and nuclear morphology, increased expression of cell adhesion markers (such as ICAM-1 and/or E-cadherin) and, in malignant breast cells, enlargement of the nuclear size and synthesis of milk components such as casein and lipids. Surprisingly, it has been found that concomitantly with one or more of these mature phenotypic changes, the HER-2/neu protein translocates (or migrates) from the membrane to the cytoplasm and/or perinuclear regions of the cell, and that this translocation is additionally associated with a transient increase in total cellular HER-2/neu content. Translocation and a transient increase in total cellular HER-2/neu content serves as one indicator of terminal cell differentiation.

In particularly preferred embodiments of the present invention, the response to antibody or ligand therapy in a patient having breast cancer or ovarian cancer is prognosticated by contacting a biopsied sample from said cancerous tissue with the monoclonal antibody or ligand selected for therapy for a predetermined time and determining, by immunohistochemical staining techniques translocation of the HER-2/neu product from the cell membrane to the cytoplasm or perinuclear region of said cancerous cell (or a transient increase in total HER-2/neu content), an increase in nuclear area and/or an increase in ICAM-1 (and/or E-cadherin) expression. Stained samples may be analyzed for optical density values which correspond to the amounts of stained cell constituents. Translocation may be determined by (1) a reduction of HER-2/neu in the surface, (2) an increase in HER-2/neu in the cytoplasm or perinuclear region, (3) a transient increase in the total HER-2/neu content, or a any combination of (1), (2) and (3). Nuclear area and expression of ICAM-1 or E-cadherin may be measured by similar immunohistochemical techniques. The malignant cells treated in accordance with a method of the invention, in the presence of absence of a putative anti-cancer agent, then are examined to determine the percentage of cells which have been induced to differentiate.

This can be determined by comparing the percentage of treated cells containing HER-2/neu predominantly in the cytoplasm and/or perinuclear region as compared to the percentage of cells in a negative control showing such a distribution of HER-2/neu product. A decrease of HER-2/neu product in the surface membrane of the treated cells, alone, or in combination with an increase in the cytoplasm or perinuclear region or an increase in the total HER-2/neu content (as compared to untreated cells) can be used to indicate induction of terminal differentiation.

Preferably, the average amount of membrane-bound HER-2/neu per cell in the control population can be used as a test value in obtaining cell percentages. The average is calculated from a statistically significant number of cells in the control group. Then, the amount of membrane-bound HER-2/neu in individual control group cells is compared to the average, to determine what percentage of the population has a lower amount of membrane-bound HER-2/neu, and what percentage has a higher amount. Cells from the treated group are similarly examined to determine what percentage of cells evidence less membrane-bound HER-2/neu than the control group average, and what percentage evidence greater membrane-bound HER-2/neu than the control group average. Finally, a comparison can be made between the percentages obtained for the control group, and the percentages obtained for the treated group. A statistically significant increase in the percentage of cells in the treated group over the percentage of cells in the control group which have less membrane-bound HER-2/neu than the control group average indicates translocation of HER-2/neu. (The same approach is followed for determining changes in nuclear area and cell adhesion molecule expression.)

The amount of cytoplasmic HER-2/neu also can be examined instead of the amount of membrane-bound HER-2/neu to obtain cell percentages as described above. A statistically significant increase in the percentage of cells in the treated group over the percentage of cells in the control group which have more cytoplasmic HER-2/neu than the control group average indicates translocation of HER-2/neu.

The total amount of cellular HER-2/neu also can be examined instead of membrane-bound cytoplasmic HER-2/neu to obtain cell percentages as described above. A statistically significant increase in the percentage of cells in the treated group over the percentage of cells in the control group which have more total cellular HER-2/neu than the control group average indicates translocation of HER-2/neu.

In an alternative embodiment, the average amount of HER-2/neu found in a sample of treated cells (by examination of optical density values after staining) can be compared to the average amount of HER-2/neu found in a sample of control cells to determine translocation. The amount compared may be only that which is membrane-bound, in which case a statistically significant decrease in staining in the treated sample indicates translocation. Alternatively, the amount compared may be only cytoplasmic, or may be the total cellular content, in which cases any statistically significant increase in staining in the treated sample indicates translocation.

The location and distribution of a cellular component, such as HER-2/neu protein, cell adhesion molecule(s), or casein or lipid droplets can be determined immunohistochemically. The cells of the biopsied sample may be fixed in a fixative, such as paraformaldehyde, followed by treatment with an organic solvent, such as acetone, formalin, or methanol, so as to render the cells permeable for immunohistological staining. Methods of fixation are well within the skill of the art. See, e.g., Bacus et al., Molec. Carcin., 3:350–62 (1990).

Where the presence and distribution of HER-2/neu and/or cell adhesion molecule(s) are to be determined, cells can be stained with an antibody specific for the HER-2/neu product and/or cell adhesion molecule conjugated to a fluorescent dye, such as fluorescein, rhodamine and the like. Where two or more different antibodies are conjugated to fluorescent dyes it is appropriate to conjugate each antibody to a fluorescent dye that fluoresces at distinguishable wavelengths. The location and distribution of HER-2/neu and/or cell adhesion molecule(s) in the cells can be determined conventionally by fluorescence microscopy, and, optionally, confirmed by confocal microscopy. Besides direct immunofluorescence staining, indirect antibody staining procedures which detect the presence of specific antigen-antibody complexes, such as peroxidase-anti-peroxidase staining procedures or alkaline phosphatase staining, may be used to determine the distribution of HER-2/neu and/or cell adhesion molecule(s) in such fixed cells.

Mature phenotype expression also can be used to determine the extent of terminal cell differentiation in the first portion of biopsy. For example, immature cancerous human breast cells and mature cells (e.g., malignant cells which were induced to differentiate) can be distinguished by the ability of the mature cells, but not the malignant cells, to produce human milk components, including casein and lipids. The percentage of cells which have been caused to differentiate in a method of the invention may be determined by the presence of such milk components. Casein can be detected by known immmunohistochemical staining using anti-casein antibodies. The presence of lipids may be detected by staining with a dye compound suitable for such detection, such as Oil Red O. See, e.g., Bacus et al., Molec. Carcin., 3:350–62 (1990).

After staining, the location of the HER-2/neu protein, for example, can be determined and a qualitative or quantitative analysis made of HER-2/neu migration (i.e., translocation). A quantified measure of the amount of the protein per cell can be taken by digitizing microscope images of stained samples, and converting light intensity values of pixels of the digitized image to optical density values, which correspond to the amounts of stained protein. See, e.g., Bacus et al., Applied Optics, 26 3280–3293 (1987).

In particular, quantification can be accomplished in the following manner. A cell culture sample is stained for the oncogene product, according to a staining procedure as described above, or some other staining procedure known in the art. The cell culture sample also is stained for DNA, such as by the Feulgen technique. The DNA stain should be distinguishable on the basis of the wavelength emitted (i.e., of different color from the stain for the protein(s) to permit differentiation between the stains). Digitization of different filtered images of the single sample image through respectively different filters, one for each specific stain, allows an optical density value to be associated with each pixel of each filtered image in a computer system programmed to process the images. The optical density of the protein stain image(s) and the optical density of the DNA stain image are summed by the computer.

The DNA stain is applied to another sample of the same cell culture, and a human operator interactively identifies individual cells to the computer, which calculates sums of optical densities for the individual cells so identified. This second image supplies the average DNA per cell. The previous sum of optical density from the first DNA stain image, representing the total DNA that was seen in that image, is divided by the average DNA per cell for the culture this yields the number of cells in the first portion. The sum of optical density for the protein then is divided by this number of cells to yield the average protein content per cell. A reference control portion of a standard cell line, not necessarily related in any way to the cells from the sample, and in which DNA content and oncogene protein content per cell are known, can be stained with identical stains and used to calibrate optical density with the mass of stained material. A fuller understanding of protein quantification and nuclear area measurement can be obtained from U.S. Pat. Nos. 4,175,860; 4,998,284; 5,008,185; 5,106,283; and 5,028,209, which are incorporated by reference.

The quantification of membrane-bound HER-2/neu (and cytoplasmic HER-2/neu) and/or cell adhesion molecule(s) preferably can be carried out by selecting for optical density summation only those pixels in the digitized images which correspond to the membrane (or the cytoplasm) or representative portions thereof. Pixel selection can be carried out by automatic computer algorithm or by human interaction.

Alternatively, membrane-bound HER-2/neu and/or cell adhesion molecule(s) can be quantified using the above-described digitzed image analysis in conjunction with fixation and staining procedures which do not make the membrane permeable to the elements of the staining complex, and thus result exclusively in staining of membrane-bound product. Briefly, for example, sample cells are fixed for 60 minutes at room temperature in 10% neutral buffered formalin. The murine monoclonal antibody TA-1 (Applied Biotechnology, Cambridge, Mass.), which is directed to the membrane-external domain of HER-2/neu, is applied typically at a concentration of 2 μg/mL. This fixation procedure does not make the cells permeable to the TA-1 antibody. Second step antibodies and stains (e.g., goat anti-mouse antibodies conjugated to a fluorescent dye) are applied with the result that only membrane-bound HER-2/neu is stained. The amount of membrane-bound HER-2/neu per cell averaged over a sample of cells is determined as described above, by image analysis and using a Feulgen stain for DNA.

Alternatively, indicia of terminal differentiation in cells subject to the method of the present invention include morphological changes in cells which are characteristic of a mature cell type. In cases where the morphological change is dramatic, such as a fundamental qualitative change in the shape or structure of a cell (or its nucleus) as viewed through a microscope, a determination of the extent of cell differentiation may be made by examining the cells under a microscope and counting the number if cells which exhibit qualitative morphological features associated with terminal cell differentiation. Malignant cells characteristically are compact and spherical with a similar nucleus which densely stains, whereas terminally differentiated cells characteristically are flattened, having a cytoplasm which exhibits a delicate lacy appearance and a diffuse nucleus. The percentage of cells displaying the latter morphological features may be used to quantify the extent of terminal cell differentiation induced by a putative therapeutic agent in a given portion of cells and consequently permit a prognosis relating to the effect of the putative therapeutic agent in the malignancy sought to be treated.

Moreover, quantitative morphological differences, such as the change in the ratio of cytoplasmic area to nucleic area which can be quantified by computerized image analysis techniques as described above, can be used to delineate between immature and mature cells.

Cell proliferation is yet another measure of the extent of terminal cell differentiation. Immature cancer cells will proliferate indefinitely whereas mature cells will not. A stabilization and reduction of cell population as compared to untreated control cells indicates substantial terminal cell differentiation. A marked difference in growth curves between treated and untreated portions also may indicate substantial terminal cell differentiation. Statistical methods for analyzing cell populations are well known in the art, and the aforementioned examples should not be taken as a limitation of the methods which may be applied to determine aspects of terminal cell differentiation within the cell population.

The invention is illustrated in the following Examples.

EXAMPLE I

Monoclonal antibodies to the HER-2/neu product were made by injecting Balb/c mice intraperitoneally 3 times (2 week intervals) with 3 to 5×10⁶ viable SKBR3 human breast cancer cells in phosphate buffered saline ("PBS"). Spleen cells of mice which developed a strong immune response were isolated and fused with NSO myeloma cells, using polyethylene glycol, and hybridomas were selected with HAT (hypoxathine/aminopterin/thymidine) medium. Hybridomas were screened for specific binding to recombinant HER-2/neu product expressed on the surface of fixed Chinese hamster ovary (CHO) cells which had been transfected with an appropriate expression vector. Monoclonal antibodies specifically binding HER-2/neu products were detected with $^{125}$I-labeled goat anti-mouse F(ab')$_2$ antibody. The antibodies that specifically bound to the transfected CHO cells were selected for further analysis using either an immuno-precipitation assay with [$^{35}$S]methionine labeled cells, or immuno-precipitation followed by auto-phosphorylation in the presence of MnCl$_2$ and [$^{32}$P]ATP. This immunization procedure elicited specific antibodies to the extracellular portion of the human HER-2/neu antigen. Four of the monoclonal antibody preparations, designated N12, N28, N24 and N29, were depositied as described above. N10 was provided by Dr. Yosef Yarden of the Weizmann Institute, Rehovot, Israel. Monoclonal antibodies N12, N24, N28 are of the IgG$_1$ subclass and the N29 monoclonal antibody preparation is of the IgG$_2$ subclass.

EXAMPLE II

N29 was purified from ascites fluid by ammonium sulfate precipitation (40% saturation) followed by chromatography on a Sepharose-Protein A column. Fractions containing the antibody were obtained by elution at low pH (50 mM citric acid at pH 4.8). The antibody preparation was homogeneously pure as determined by gel electrophoresis under reducing conditions. SDS-polyacrylamide gel-separated heavy and light chains were transferred to polyvinylidene difluoride membranes and subjected to Edman degradation. Amino acid sequences of the amino termini of both the heavy and the light chains (20 amino acids of each) were thus obtained, as follows:

H. chain:

Glu Val Gln Leu Val Glu Ser Gly Gly Gly Leu Val Gln Pro Lys Gly Ser Leu Lys Leu (SEQ ID NO:1)

L. chain:

Asp Ile Val Met Thr Gln Ser Gln Lys Phe Met Set Thr Set Val Val Asp Arg Ile Ser (SEQ ID NO:2)

In order to characterize the antibodies N12, N24, and N29, the following experiments were performed.

HER2 cells were plated in 24-well plates and assayed at confluence. Confluent monolayers of the HER2 cells were incubated for an hour at 22° C. with various concentrations of antibodies in PBS containing 1% bovine serum albumin (BSA). After washing with the same buffer, the cells were incubated for 90 minutes with $I_{125}$-labeled goat anti-mouse F(ab')$_2$ to determine bound antibodies. The cells then were washed, solubilized with 0.1M NaOH, and the radioactivity determined in a gamma counter. Control cells were incubated in the absence of the murine antibody and their background binding was subtracted.

FIG. 1 shows the binding of the five antibodies to the HER2 cells: N10 (Δ), N12 (·), N24 (o), N28 (▲) and N29 (■). All specifically bound to cultured cells that express HER2/neu with different apparent affinities. N28 and N24 displayed the highest apparent affinity whereas N10 exhibited the lowest apparent affinity.

HER2 cells were metabolically labeled with [$^{35}$S]methionine and the cell lysates were separately subjected to an immunoprecipitation assay with 10 μg of each antibody. As a control, an irrelevant antibody, anti-dinitrophenol (anti-DNP), was used. Proteins were separated on a SDS-7.5% polyacrylamide gel. The results are shown in FIG. 2A.

The immunoprecipitation assay was performed as described in Example I but with unlabeled cells. Prior to electrophoresis, the proteins from the cell lysate were labeled by autophosphorylation with gamma[$^{32}$P]ATP and 10 mM MnCl$_2$. Autoradiograms are shown: NI (non-immune serum), PolyCl (polyclonal anti-HER2/neu antibody). The results are shown in FIG. 2B.

Figure 2A:
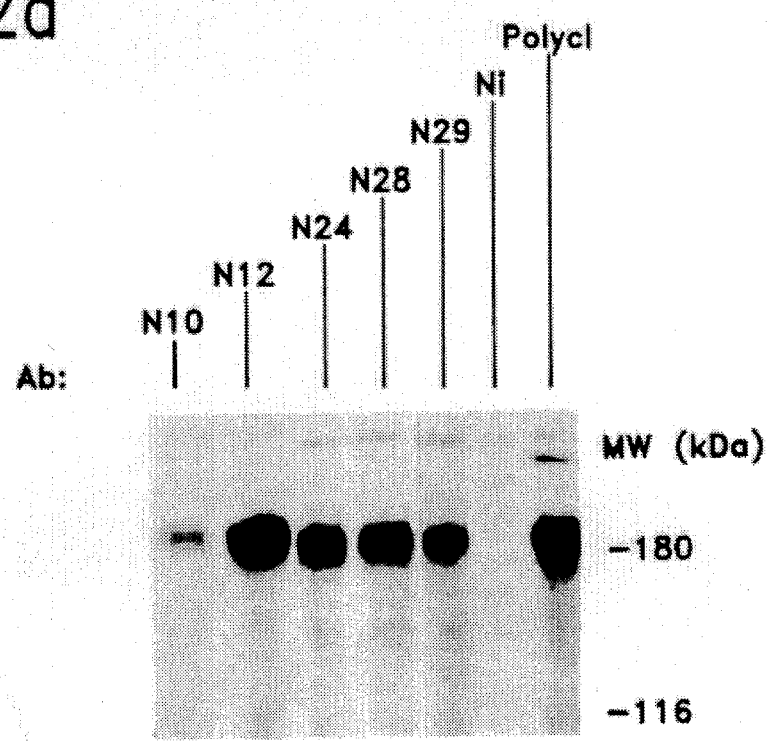
FIGS. 2A and 2B illustrate immunoprecipitation of the HER2/neu protein by various monoclonal antibodies. Panel A illustrates immunoprecipitation with HER2 cells labeled with [$^{35}$S]methionine and Panel B a Kinase assay.
Figure 2B:
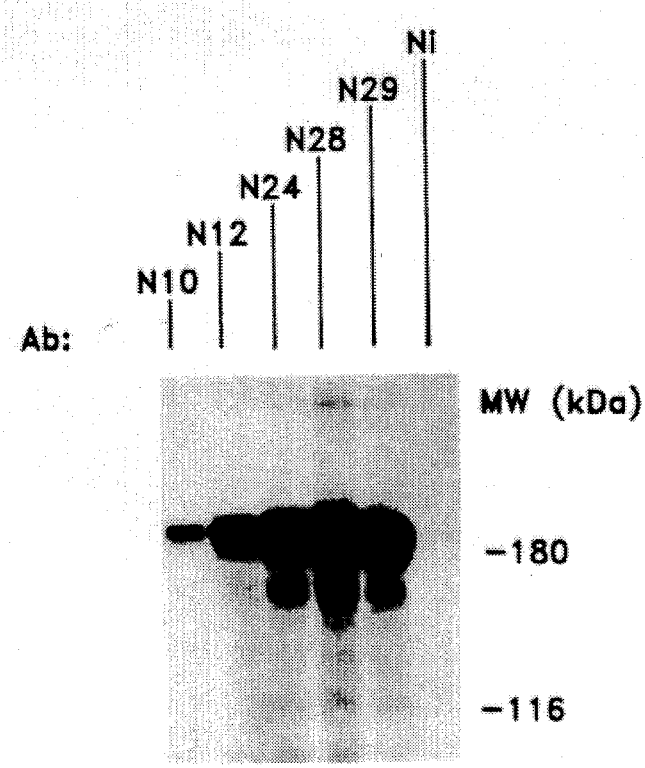

All immunoprecipitated a single protein of 185kD from metabolically labeled HER2 cells, as shown in FIG. 2A. This also was reflected in an in vitro kinase assay performed on the immunoprecipitates (FIG. 2B). None reacted with EGFR or with the rat p185$^{neu}$. Western blot analysis of the HER-2/neu protein showed that only N12 and N29 were capable of reacting with the denatured form of the receptor. (See Table I). For the Western blot analysis, HER2 cell lysates were separated by SDS-PAGE, transferred to nitrocellulose, and blotted with the antibodies, followed by detecting using horseradish peroxidase conjugated goat anti-mouse F(ab')$_2$.

The antibodies also were assayed for their ability to affect tumor growth of murine fibroblasts transformed by overexpression of HER2/neu in athymic mice. HER2 cells (3×10⁶) were injected subcutaneously into CD1/nude mice. The antibodies or a control (an irrelevant antibody to dinitrophenol or PBS) were injected intraperitoneally, into groups of 5 nude mice, on days 3, 7 and 10 after tumor inoculation. Tumor parameters were measured twice a week with callipers, and tumor volume was calculated according to the

TABLE I

| Ab | Western Blot | Tumor Growth | Cell Prolif. | CDC | ADCC | Tyrosine Phosphoryl. | Receptor Degradation |
|---|---|---|---|---|---|---|---|
| anti-DNP | − | 100 | 100 | ND | ND | 1.0 | 6.5 |
| N10 | − | 54 | 247 | 68 ± 3.1 | 7 ± 1 | 0.9 | 6 |
| N12 | + | 2 | 63 | 9 ± 0.9 | 10 ± 0.01 | 1.8 | 6 |
| N24 | − | 16 | 196 | 60 ± 1.1 | 9 ± 2.2 | 2.5 | 3.5 |
| N28 | − | 141 | 107 | 10 ± 1.7 | 18 ± 0.01 | 14 | 3 |
| N29 | + | 0.3 | 72 | 9 ± 2.2 | 12 ± 0.33 | 1.2 | 2.5 |

TABLE I-continued

| Ab | Western Blot | Tumor Growth | Cell Prolif. | CDC | ADCC | Tyrosine Phosphoryl. | Receptor Degradation |
|---|---|---|---|---|---|---|---|

ND = Not Determined formula: tumor volume=length×width×height. In order to validate volume measurements, the correlation between the tumor volume and tumor weight was determined on the day of animal killing. The results are shown in Table 1 (average tumor volume as percentage of control wherein "100" equals the control value; n=5, measured 21 days after tumor inoculation) and in FIG. 3.

Figure 3A:
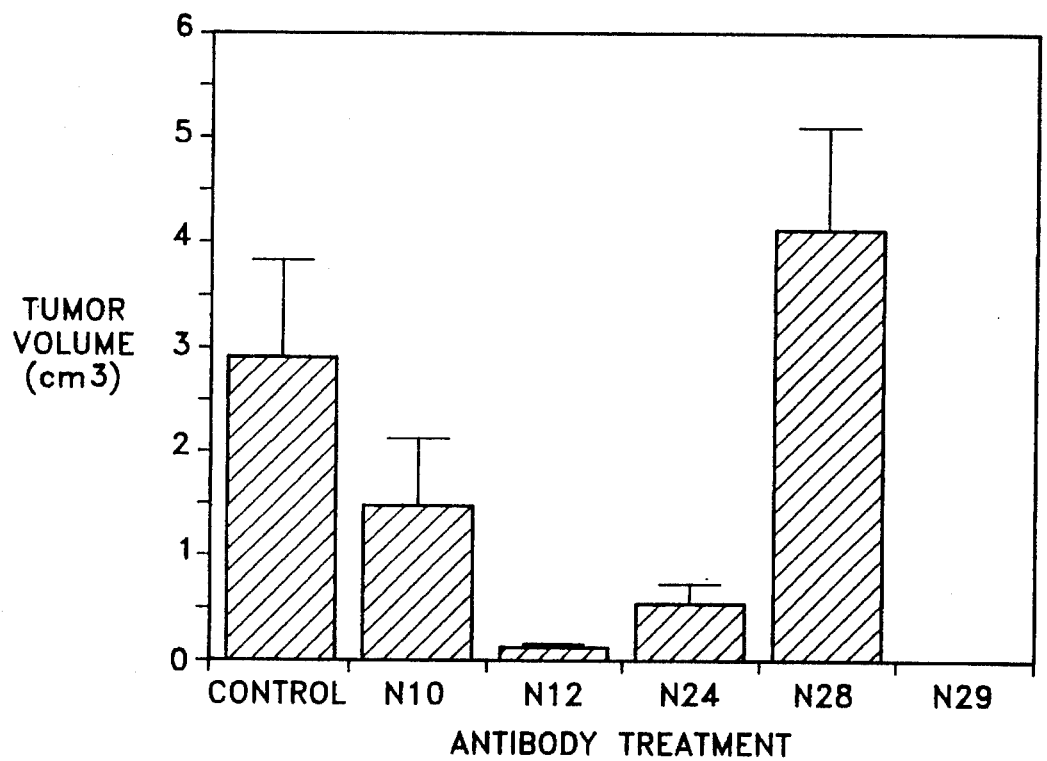
FIGS. 3A and 3B illustrate the effect of various monoclonal antibodies on tumor growth in athymic mice. Panel A shows the effects of antibody treatment after 21 days post-inoculation. Panel B illustrates the kinetics of tumor growth in antibody-induced athymic mice.

FIG. 3A depicts tumor volumes of each group of mice, on day 21, post inoculation, after treatment. The tumorigenic growth of HER2 cells was significantly inhibited ($P < 0.05$ as calculated using the Anova and Duncan's multiple comparison test) in nude mice that were injected with N29, and N12, when compared with mice that received no antibody or the control anti-DNP antibody.

Figure 3B:
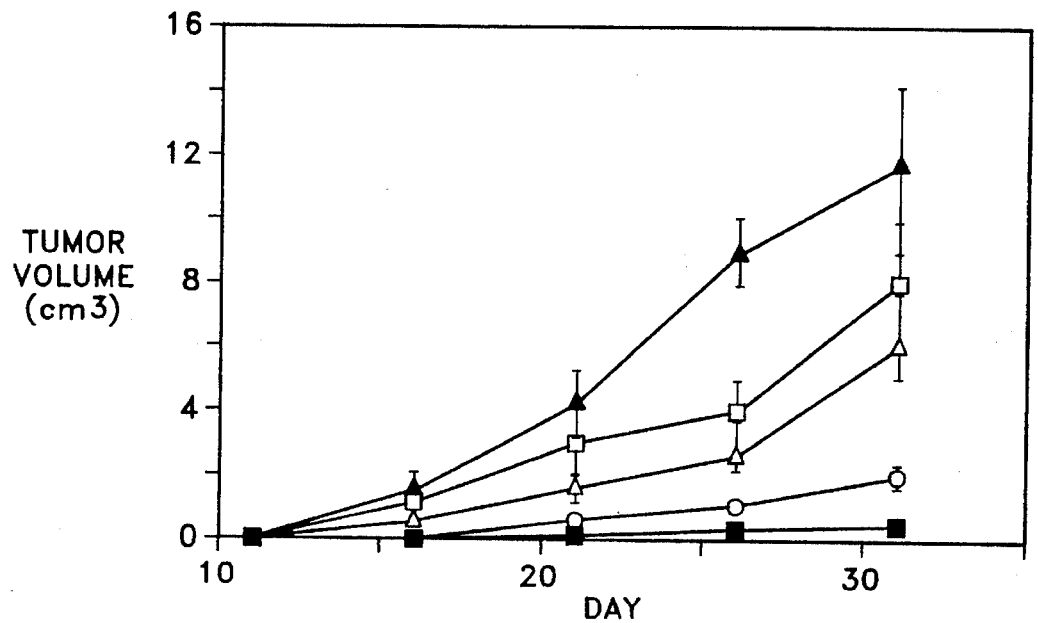

FIG. 3B depicts the kinetics of tumor growth in antibody treatment mice: control (□), N10 (Δ), N12 (·), N24 (o), N28 (▲), N29 (■). It can be seen that the inhibitory effect of the antibodies persisted over 31 days after tumor injection. Antibodies N10 and N24 exhibited less efficient inhibition of tumor growth. In contrast, monoclonal antibody N28 consistently stimulated tumor growth. Essentially identical results were obtained in three separate experiments.

To test the possibility that the effects seen in vivo are reflected in vitro, cell proliferation assay in culture and cytotoxicity assay with the antibodies were performed on SKBR3 human breast carcinoma cell line (from the American Type Culture Collection).

In the cell proliferation assay, SKBR3 cells were plated in 24-well plates $10^3$ cells/well and incubated for 48 h in medium supplemented with 10% fetal calf serum. The amount of serum was then decreased to 5% and the indicated antibodies added at 10 µg/ml concentration. Five days later, the number of viable cells was determined. The results (in percentage) are shown in Table 1 wherein "100" equals the amount of cell proliferation for control treatment.

Complement-dependent cytotoxicity ("CDC") assay of SKBR3 tumor cells was performed as follows: the SKBR3 tumor cells were incubated at 37° C. for 2 hours, in a volume of 0.1 ml fetal calf serum, with 300 µCi of Na[$^{52}$Cr]O$^4$ (New England Nuclear). At the end of the labeling period the cells were washed three times in PBS and $1.5 \times 10^4$ cells were plated in each well of a 96-well microtiter plate.

Various concentrations of the antibodies were added, and incubated with the cells for 1 hour, followed by the addition of human or rabbit complement and incubation for further 3 hours. Appropriate control wells containing cells alone, cells with no antibody, or no complement, and cells lysed in 10% SDS were set up in parallel. The results also are shown in Table 1. Values represent [$^{51}$Cr]O$_4$ release (determined in a gamma counter) from cells treated with the indicated antibodies (50 µg/ml) as percentages of total cellular content of [$^{51}$Cr]. The means of triplicate determinations are given. Corrections were made for spontaneous release, in the absence of antibody and complement.

Antibody-mediated cell-dependent cytotoxicity ("ADCC") assay was performed as follows: the SKBR3 tumor cells were labeled with Na[$^{51}$Cr]O$_4$ as described above. $5 \times 10^3$ cells in 25 µl were incubated for 1 hour with various concentrations of the antibodies, and then for 5 hours with effector cells, human peripheral blood lymphocytes (0.1 ml, lymphocytes: tumor cells=140:1), or with mouse splenocytes (120:1). [$^{51}$Cr] release was determined as described above. The results in Table 1 express percentages of the antibody-mediated cell-dependent lysis of SKBR3 cells using 50 µg/ml of each antibody in the assay.

Two different assays were employed to test the capacity of the monoclonal antibodies to elevate tyrosine phosphorylation of the HER-2/neu protein: HER2 cells were metabolically labeled with [$^{32}$P]orthophosphate, incubated with the antibodies and subjected to two consecutive immunoprecipitation steps with anti-phosphotyrosine and anti-HER-2/neu antibodies, as described by Yarden et al., Proc. Natl. Acad. Sci., 86: 3179–3183 (1989). Alternatively, SKBR3 cells were first incubated with the antibodies and then subjected to two consecutive immunoprecipitation steps, followed by an in vitro phosphorylation assay in the presence of gamma ($^{32}$P)ATP and MnCl$_2$.

The SKBR3 and HER2 cells were grown in a 24-well plate and labeled for 4 h in Dulbecco's modified Eagle medium (DMEM) without phosphate, but in the presence of 1% dialyzed fetal calf serum ("FCS") and [$^{32}$P]orthophosphate (0.5mCi/ml). The cells were washed with PBS and incubated for 15 min at 22° C. with fresh medium containing antibodies at a concentration of 10 µg/ml. After washing, the cells were lysed in solubilization buffer (50 mM Hepes, pH 7.5; 150 mM NaCl; 10% (vol vol) glycerol; 1% Triton X; 1 mM EDTA; 1 mM EGFR; 1.5 mM MgCL$_2$; 2 mM PMSF; 1% Aprotinin, 1% Leupeptin (added just before use and the tyrosine phosphorylated HER2/neu protein was immunoprecipitated with an agarose-immobilized antibody to phosphotyrosine (Hung et al., Proc. Natl. Acad. Sci., 84: 4408–4412 (1987)). The immuno-complexes were eluted with solubilization buffer containing 50 mM p-nitrophenylphosphate and subjected to immunoprecipitation with a rabbit polyclonal anti-HER-2/neu antibody, directed to the carboxy terminus of the protein.

Figure 4A:
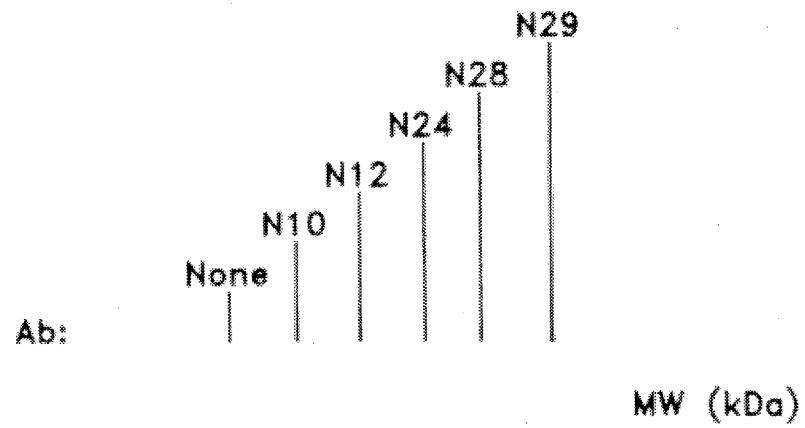
FIGS. 4A and 4B depict antibody-induced stimulation of tyrosine phosphorylation of the HER2/neu product. The autoradiograms of the SDS-gel separated proteins obtained in two different tyrosine phosphorylation assays are shown. In Panel A HER2 cells labeled with [$^{32}$P]orthophosphate were incubated with each antibody, and subjected to two consecutive immunoprecipitation steps with anti-phosphotyrosine and anti-HER2/neu antibodies. In Panel B, SKBR3 cells were first incubated with various monoclonal antibodies and then subjected to two immunoprecipitation consecutive steps, followed by autophosphorylation with gamma [$^{32}$P]ATP and $Mn^{2-}$.

According to the first assay, monolayers of HER2 cells were labeled with [$^{32}$P]orthophosphate and then incubated for 15 min at 22° C. with 10 µg/ml of each antibody. Tyrosine phosphorylated proteins were immunoprecipitated with an anti-phosphotyrosine antibody, followed by specific elution and a second immunoprecipitation step with the rabbit anti-HER-2/neu polyclonal antibody. The extent of induction of tyrosine phosphorylation of the HER-2/neu protein by the antibodies was determined by densitometry of autoradiograms. The results are shown in Table I and in FIG. 4A.

Figure 4B:
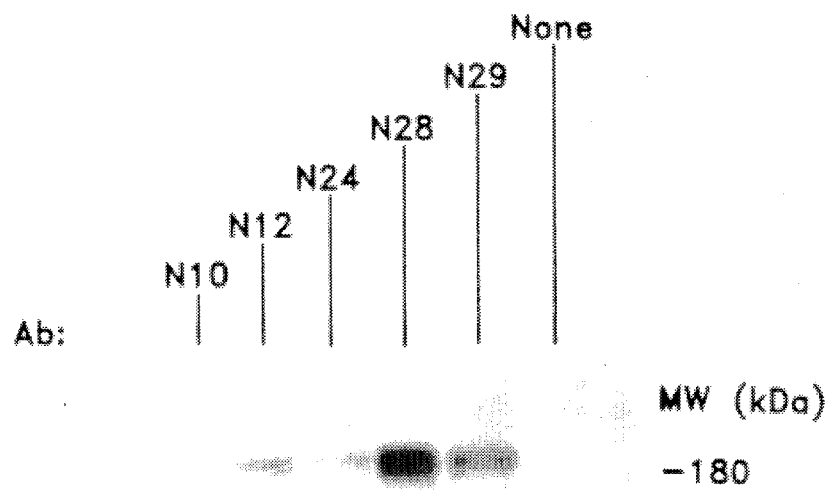

In the second assay, SKBR3 cells were first incubated with the antibodies, immunoprecipitated in two consecutive steps, as described above, and labeled by autophosphorylation with gamma [$^{32}$P]ATP and Mn$^{2-}$. The autoradiograms of the SDS gel separated proteins are shown in FIG. 4B.

Similar results were obtained in both analyses: NB28 significantly stimulated phosphorylation of the HER-2/Neu product on tyrosine residues, whereas the other antibodies displayed low or no activity (N10) in living cells.

The interaction of receptor tyrosine kinases with their respective ligands is usually coupled to rapid endocytosis. The potential of the antibodies to the human HER-2/neu protein to accelerate the turnover of the receptor was tested. For this purpose, HER2 cells were biosynthetically labeled with radioactive methionine, and then chased for various periods of time with fresh medium that contained different antibodies. At the end of the chase period, the residual labeled protein were immunoprecipitated and analyzed by gel electrophoresis and autoradiography.

SKBR3 or HER2 cells were grown in 24-well plates to 80% confluence, and then labeled for 16 hours at 37° C. with [$^{35}$S]methionine (50 µCi/ml). After washing with PBS, the cells were incubated with fresh medium in the absence or presence of the antibodies (at a concentration of 10 µg/ml), for various periods of time. The cells then were washed and cell lysates were subjected to immunoprecipitation with a rabbit polyclonal antibody to the HER2/neu protein. The results expressed as the half-life of the labeled protein ($t_{1/2}$) are shown in Table I.

Figure 5:
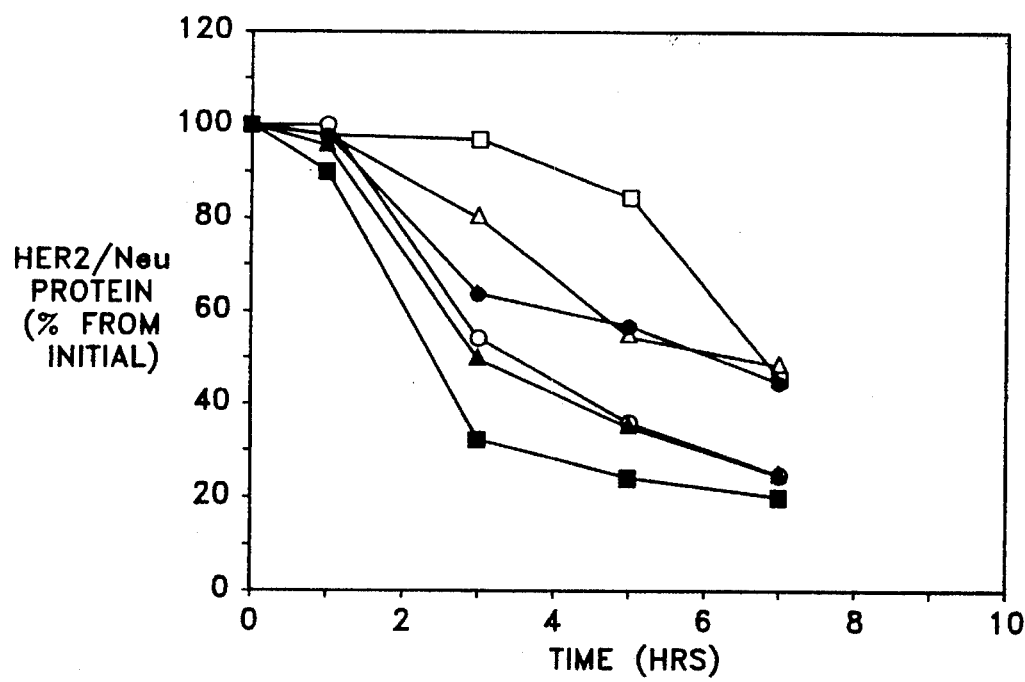
FIG. 5 illustrates the effect of various monoclonal antibodies on the rate of turnover of the HER2/neu protein.

FIG. 5 shows the effect of the antibodies on the rate of turnover of the HER-2/neu product. HER2 cells were labeled with [$^{35}$S]methionine in a 24-well plate and then chased for the indicated period of time with fresh medium that contained the indicated antibodies. Residual $^{35}$S-labeled HER-2/neu protein was subjected to immunoprecipitation with the rabbit polyclonal antibody and separated on a SDS-gel. Quantitative analysis of receptor turnover is shown, as determined by measuring the densitometry of the autoradiogram. Control cells without antibody treatment (□), N10 antibody treated cells (Δ), N12 (·), N24 (o), N28 (▲), and N29 treated cells (■). As shown in FIG. 5, all the antibodies accelerated, to different extents, the rate of turnover of the receptor, with antibody N29 being the most effective.

Conjugates of ricin A and antibodies N24 and N29 were prepared by covalent crosslinking with the bifunctional reagent SPDP (succinimidyl-3 2-pyridyldithiopropionate). Unbound ricin was separated by gel filteration on Sephadex G100. The conjugates were purified by passage on Blue Sepharose CL-6B (removal of unsubstituted antibody).

Figure 6:
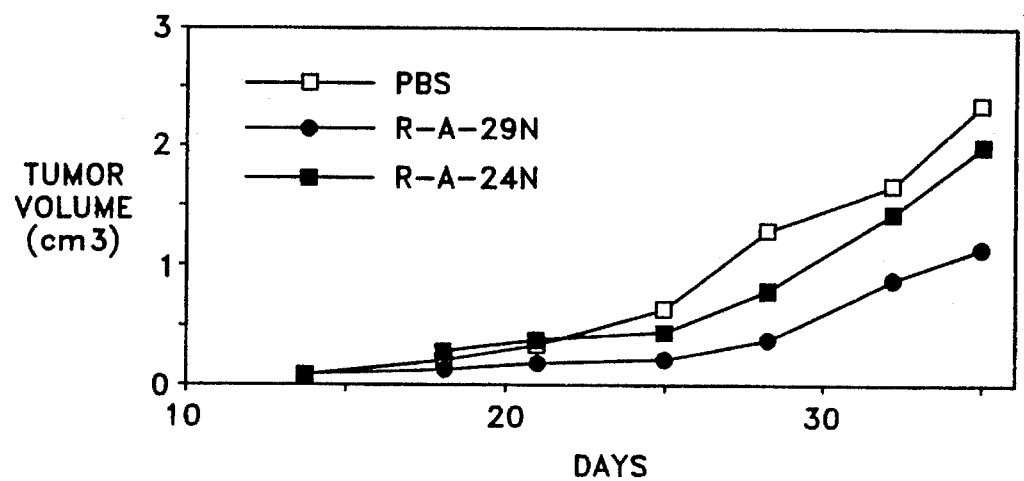
FIG. 6 depicts retardation of tumor growth by conjugates of antibodies N24 and N29 with ricin A.

The conjugates were assayed for their ability to affect tumor growth as described above, for this purpose, CD1 nude female mice received HER2 tumor cells ($3.2 \times 10^6$) injected subcutaneously. Eleven days later a single injection of Ricin A—antibody conjugate was injected intravenously. RicinA-N24: 3.9 µg Ricin A Sound to 65 µg of antibody. Ricin A-N29: 4 µg Ricin A bound to 90 µg of antibody. The tumor size was measured every 3–4 days, during 40 days. The results are depicted in FIG. 6, showing retardation of tumor growth by both conjugates Ricin A—N24 antibody and Ricin A—N29 antibody.

EXAMPLE III

Human breast cancer cell lines, AU-565, MDA-MB 543 and MCF-7, are well known in the art and widely available. The AU-565 cell line overexpresses both HER-2/neu and EGFR, MDA-MB 453 cells overexpress HER-2/neu; MCF-7 cells do not overexpress HER-2/neu. In each case cultured cells of the respective cell lines trypsinized, pelleted and seeded into four chamber slides (Nunc, Naperville, Ill.) at $0.5 \times 10^4$ The AU-565 cells were obtained from Naval Biosciences Laboratory in Oakland, Calif. Cultures of MCF-7 cells (ATCC accession no. MCF-7 HTB 22) and MDA-MB 543 (ATCC accession no. 453 HTB 131) were obtained from the American Type Culture Collection in Rockville, Md.

The cells were cultured in RPMI 1640 supplemented with 20% fetal bovine serum, penicillin (100 µg/mL) and streptomycin (100 µg/mL) in a humidified incubator with 8% $CO_2$ in air at 37° C. One day after seeding, when the cells were approximately 10%–20% confluent, the cell culture medium cells were supplemented with 10 µg/mL of one of the following monoclonal antibody preparation having specificity for the extracellular domain of the HER-2/neu protein: N12, N24, N28 and N29, control IgG (an irrelevant IgG antibody). Also, PBS alone was added to certain control cultures as a control in which IgG was absent. The cells were cultured for an additional 4 days and then examined to determine the efficacy of the respective monoclonal antibody preparation with respect to inducing the malignant breast cells to undergo terminal cell differentiation. Differentiation was assayed by the percentage of cells producing lipid, cell numbers, nuclear area per cell ($\mu m^2$) and the translocation of HER-2/neu as evidenced by total cellular content of the protein (where 100% expression equals amount HER-2/neu in sparsely growing untreated cells) and human identification of the location of staining in confocal microscopy. The results shown in Table 2 relate to the AU-565 cell line.

TABLE II

| Ab | Cell # $10^4/cm^2$ | HER-2/neu | Nuclear area | % Cells lipid | % Cells casein |
|---|---|---|---|---|---|
| Cont. | 6.0 | 103 | 100 | 12 | 20 |
| IgG | 6.3 | 84 | 101 | 7 | 20 |
| N12 | 5.6 | 154 | 121 | 40 | >90 |
| N24 | 7.1 | 152 | 147 | 52 | >90 |
| N28 | 8.6 | 104 | 102 | 8 | <30 |
| N29 | 4.8 | 160 | 154 | 55 | >90 |

The data above indicates that monoclonal antibodies N29, N24 and N12 induced the malignant breast cells to undergo differentiation and exhibit mature phenotypic traits, whereas the N28 antibody, which also has specific binding affinity for a portion of the extracellular domain of the HER-2/neu product, actually promoted the tumorigenicity of the treated AU-565 cells. Confocal microscope images showed that treatment of AU-565 cells with N28 antibody did not result in a translocation of the HER-2/neu protein from the membrane, while translocation from the membrane to the cytoplasm and perinuclear region of the cells was demonstrated in AU-565 cells treated with the N29, N24 and N12 monoclonal antibodies.

Results for the MDA-MB 543 cells line were similar to results for the AU-565 cell. The MCF-7 cells, which did not overexpress HER-2/neu, were largely unaffected by the antibodies, except that monoclonal antibody N29 increased the percentage of cells exhibiting lipid droplets.

Phenotype expression as a marker of terminal cell differentiation was measured by detecting the production of lipid droplets and casein, both of which are components of human milk. Lipid droplets were detected by a modified "Oil Red O in propylene glycol" method. D. C. Sheehan, *Theory and Practice of Histotechnology*, p. 209, C. V. Mosby Company, St. Louis, (2nd ed. 1980). For the lipid staining procedure, the culture medium was removed, the cells were rinsed with 0.05M phosphate buffered saline, pH 7.6, and fixed by a quick dip in −20° C. methanol/acetone. After fixations, the slides on which the cells were grown were placed in absolute propylene glycol for 2 minutes at room temperature in an Oil Red O staining solution. The slides then were dipped in 85% isopropanol, rinsed with deionized water, counterstained in Mayer's hematoxylin, blued in saturated lithium carbonate, and covered with glycerol jelly.

The presence of casein was detected by histochemical staining with a mouse monoclonal antibody to human β or κ casein. After the medium was removed, cell slides were rinsed with PBS, and the cells were fixed in ethanol-formol solution at room temperature for 10 minutes. After nonspecific binding was blocked with 20% goat serum for 20 minutes at room temperature, the cells were incubated with the anti-casein (β and κ) antibody (1:250 dilution) at room temperature for 60 minutes. The slides were then rinsed with 0.5M Tris-buffered saline (TBS), pH 7.6, and then incubated with biotinylated goat anti-mouse IgG (Jackson Labs, West Grove, Pa.) at 1:200 dilution for 30 minutes. The cells were rinsed with TBS, and streptomycin conjugated alkaline phosphatase (Jackson Labs) at 1:200 dilution was applied to the cells for 30 minutes. The cells were rinsed again with TBS and incubated for 15 minutes with CAS Red (Cell Analysis Systems, Elmhurst, Ill.) as the chromogen. The cells were then counterstained with CAS DNA stain (Cell Analysis Systems).

The localization of the HER-2/neu product (i.e., translocation of HER-2/neu) was determined using confocal microscopy after immunofluorescence staining. For determination of translocation, after the culture media was removed and the cells were rinsed with PBS, the cells were made permeable with 95% ethanol for 10 minutes. Following a TBS rinse, the cells were post-fixed in 10% neutral buffered formalin for 30 minutes. After a deionized water wash, the cells were stained for DNA with a Feulgen stain, whereupon they were rinsed well with TBS (pH 7.6). After a 20 minute block with 20% normal goat serum, one portion of the cells (the other portion served for an estimate of the average DNA content of the cells, described below) was incubated with a polyclonal antibody to the C terminus of the HER-2/neu protein (Oncogene Kit from Cell Analysis Systems) for 60 minutes at room temperature. The cells then were rinsed with TBS, and incubated with a first linking antibody, mouse anti-rabbit IgG at a protein concentration of 10 mg/L (Jackson Laboratories) for 30 minutes. The dichlorotriazinyl amino fluorescein [DTAF]-conjugated goat anti-mouse IgG (Jackson Labs) was applied at a dilution of 1:100 for 30 minutes at room temperature. The cells then were rinsed with TBS, and coverslipped with gelvatol. Localization was determined using a Bio/Rad MRC-600 confocal scanning microscope adapted with a fluorescein filter. Confocal optical sections were recorded at 1μ intervals with 10 times averaging per image.

A CAS 200 Image Analyzer (Cell Analysis Systems), a microscope-based, two color image analyzing system, was used in the quantification of the HER-2/neu protein. Both solid state imaging channels of the CAS 200 Image Analyzer were used. Digitized light intensity values were converted to optical density values and added together, the result corresponding by the Lambert-Beer Absorption Law to the amounts of stained cell constituents. The two imaging channels were specifically matched to the two components of the stains used. One channel was used for quantifying the total DNA of the cells in the field following Feulgen staining with a DNA staining kit and the other for quantifying the total HER-2/neu protein of the cells in the field following immunostaining.

A separate preparation of cells from the same culture the second portion) was stained only for DNA. A human operator identified individual cells to the apparatus, and optical densities of the pixels associated with each cell were summed. Summed optical densities for each cell as well as a count of the number of cells were produced. This supplied the total DNA amount per cell for the culture.

Since the total DNA amount per cell was known from this second sample, the average total HER-2/neu protein per cell could be computed from the data of the first sample, which had been stained for both DNA and HER-2/neu. Sparsely growing AU-565 cells were used for calibrating the HER-2/neu protein content. The level of staining in such cells was defined as 100%. A complete description of this quantification is available in Bacus et al., Arch. Pathol. Lab. Med., 114: 164–169 (1990). Cell numbers were determined by hemocytometer chamber counting, and viability was monitored by trypan blue dye exclusion.

According to the method of treatment and analysis described above, the N29 antibody was found to be the best differentiation inducer. Treatment of AU-565 cells for four days with 10 μg/mL N29 antibody doubled the proportion of cells with flat morphology, and increased the nuclear area of the cells on average to 154 μm$^2$ over the control cell nuclear area of 100 μm$^2$. The fraction of morphologically mature AU-565 cells increased from 10–20% in the untreated cells to more than 90% in the cells treated with N29 antibody. The fraction of 565 cells treated with N29 antibody which contained lipid droplets was 55%, compared to 12% in the untreated control. The fraction of N29-treated AU-565 cells staining positively for the presence of casein after four days was more than 90%, compared to 20% for the untreated control. The population of N29-treated AU-565 cells was $4.8 \times 10^4$ untreated cells.

Incubation of AU-565 cells with N29 antibody resulted in a decrease in membrane staining for HER-2/neu which was accompanied by diffuse cytoplasmic localization of the protein. Quantification of the staining revealed that the redistribution involved a transient increase in total cellular HER-2/neu content. Confocal microscope images confirmed the immunohistochemical staining results. The protein migrated from the membrane and localized in the cytoplasm and in particular the perinucleus upon treatment with N29 antibody.

Treatment of MDA-MB 543 cells with N29 antibody (data not shown) elicited a marked growth inhibition of 60%, and an increase in cells positive for differentiation markers: 90% of treated cells stained positively for lipid droplets, and 70% of treated cells stained positively for casein. Treatment of MCF-7 cells with N29 antibody increased the fraction containing lipid droplets and casein to about 90%, compared with 2% in the untreated control portion. N29 had only a small growth inhibition effect on MCF-7 cells.

EXAMPLE IV

Cells of the AU-565 cell line were treated with 1 μg/ml, 3 μg/ml and 10 μg/ml of the N12, N24, N28 or N29 antibodies for a period of four days as described in Example III. An unrelated IgG (10 μg/ml) was used as a control. Staining for lipid droplets and HER-2/neu, as well as quantification of HER-2/neu by optical density values, nuclear area (μm$^2$) and determination of localization of the protein also were carried out as in Example III. The results are shown in Table III.

Again, N29 antibody showed the best efficacy in inducing differentiation. The N29 antibody preparation demonstrated a dose-dependent differentiation-inducing effect at concentrations as low as 1 μg/ml. Again, sparsely growing AU-565 cells were used for calibrating the level of HER-2/neu in the cells. The level of staining in these cells was defined as 100%.

TABLE III

| Ab | Cell # 10⁴/cm² | HER-2/neu | Nuclear area | % Cells lipid | Conc. μg/ml |
|---|---|---|---|---|---|
| Control. | 6.2 | 89 | 111.5 | 28 | |
| IgG | 6.1 | 95 | 117.4 | 19 | |
| N29 | 4.8 | 119 | 144.2 | 53 | 1 |
| N12 | 6.0 | 85 | 101.3 | 18 | 1 |
| N24 | 5.6 | 102 | 136.0 | 48 | 1 |
| N28 | 6.1 | 86 | 114.7 | 31 | 1 |
| N29 | 4.1 | 136 | 166.5 | 73 | 3 |
| N12 | 5.5 | 90 | 119.4 | 38 | 3 |
| N24 | 4.9 | 105 | 156.1 | 57 | 3 |
| N28 | 7.4 | 101 | 119.0 | 22 | 3 |
| N29 | 3.6 | 124 | 167.2 | >90 | 10 |
| N12 | 5.3 | 104 | 117.3 | 61 | 10 |
| N24 | 4.4 | 95 | 156.6 | 69 | 10 |
| N28 | 8.0 | 117 | 117.0 | 17 | 10 |

EXAMPLE V

Human breast cancer cell line AU-565 was cultured as in Example III above, and incubated with the widely available TA-1 monoclonal antibody. Incubation with the TA-1 monoclonal antibody was initiated 24 hours after cell inoculation. From 15%–20% of the cells in the control cultures exhibited a mature phenotype, characterized by large, lacy nuclei, and a spread cytoplasm containing sizeable lipid droplets. Incubation of AU-565 cells for 2 days with 1 μg/mL TA-1 resulted in a three dimensional pattern of cell growth with an increased fraction of cells having mature phenotype. On the fourth day, the number of cells in the treated portion decreased by 60% relative to the control, and the fraction of mature cells increased from the range of 15–20% to the range of 50%–60%.

Immunohistochemical staining for lipid droplets and nuclear area ($\mu^2$) were performed as in Example III. Cell numbers were determined by hemocytometer chamber counting. Results are shown in Table IV:

TABLE IV

| Ab | Cell # 10⁴/cm² | Nuclear area | % Cells lipid | Conc. μg/ml |
|---|---|---|---|---|
| Control | 5.7 | 100 | 23 | 0.0 |
| IgG | 5.1 | 96 | 16 | 1.0 |
| TA-1 | 3.0 | 156 | 33 | 0.5 |
| TA-1 | 2.3 | 160 | 48 | 1.0 |

EXAMPLE VI

A 30kD factor, gp30, secreted from MDA-MB-231 human breast cancer cells has been shown to be a ligand for the HER-2/neu product, a 185kD transmembrane receptor (also known as p185$^{HER-2/neu}$) encoded by the HER-2/neu oncogene.

Briefly, gp30 can be isolated from the conditioned media of MDA-MB-231 cells low-affinity chromatography on a heparin-Sepharose column. Fractions containing active gp30 may be detected by the ability of gp30 to bind EGFR on the cell membranes of A431 cells or MCF-7 cells. Fractions containing gp30 activity which are obtained after heparin-Seraphose chromatography may be then chromatographed by reverse-phase chromatography on a Bondapak C₃ column equilibrated on 0.05% trifluoroacetic acid and eluted with a step gradient of acetonitrile and then rechromatographed, in a second round of reverse-phase chromatography on the Bondapak C₃ column (equilibrated in 0.05% trifluoroacetic acid), where elution is with a narrow gradient of acetonitrile.

The gp30 used in Example VI was dissolved in PBS and filtered. The protein concentration of the ligand solution was confirmed after the filteration step.

Malignant breast cells of each of the three cell lines, AU-565, MDA-MB 543 and MCF-7, were seeded and cultured as described in Example III. The culture media was supplemented with 0.0, 0.3, or 6.0 ng/mL of gp30 instead of the monoclonal antibody preparations. The methods for determining the presence of lipids droplets, nuclear area ($\mu m^2$) and cell number were all carried out as described in Example III.

Treatment of AU-565 cells with various doses of gp30 inhibited cell growth in a dose-dependent fashion, in the nanogram range. Treatment of AU-565 cells with 6 ng/mL for four days resulted in about 40% growth inhibition. Treatment of MDA-MB 543 cells for four days with 6 ng/ml of the ligand gp30 resulted in 42% growth inhibition compared to the untreated control. Similar treatment of MCF-7 cells resulted in no inhibition of growth. These results are shown in Table V.

TABLE V

| Cell Line | Cell # 10⁴/cm² | Nuclear area | % Cells lipid | Conc. ng/ml |
|---|---|---|---|---|
| AU-565 | 4.0 | 96.0 | 15 | 0.0 |
| | 5.3 | 162.0 | 28 | 0.3 |
| | 2.4 | 204.0 | 76 | 6.0 |
| MDA-MB 453 | 3.4 | 65.3 | 20 | 0.0 |
| | 2.9 | 77.8 | 62 | 0.3 |
| | 2.0 | 113.1 | 84 | 6.0 |
| MCF-7 | 11.0 | 252.0 | <1 | 0.0 |
| | 11.0 | 251.0 | <2 | 0.3 |
| | 11.0 | 277.0 | 5 | 6.0 |

At the time of treatment, about 7% of AU-565 cells, 10% of MDA-MB 543 cells, and less than 1% of MCF-7 cells for 4 days with 6 ng/mL gp30 increased the fraction of cells having lipid droplets to 76%, whereas 15% of the control cells had lipid droplets. With respect to MDA-MB 543 cells, treatment for four days with 6 ng/mL gp30 increased the percentage of cells exhibiting lipid droplets to 84%, whereas 20% of the control cells exhibited lipid droplets. Similar treatment of MCF-7 cells (which do not express HER-2/neu) resulted in at most about 5% of the cells exhibiting lipid droplets, while less than 1% of control MCF-7 cells (0.0 ng/mL gp30) exhibited lipid droplets.

Figure 7:
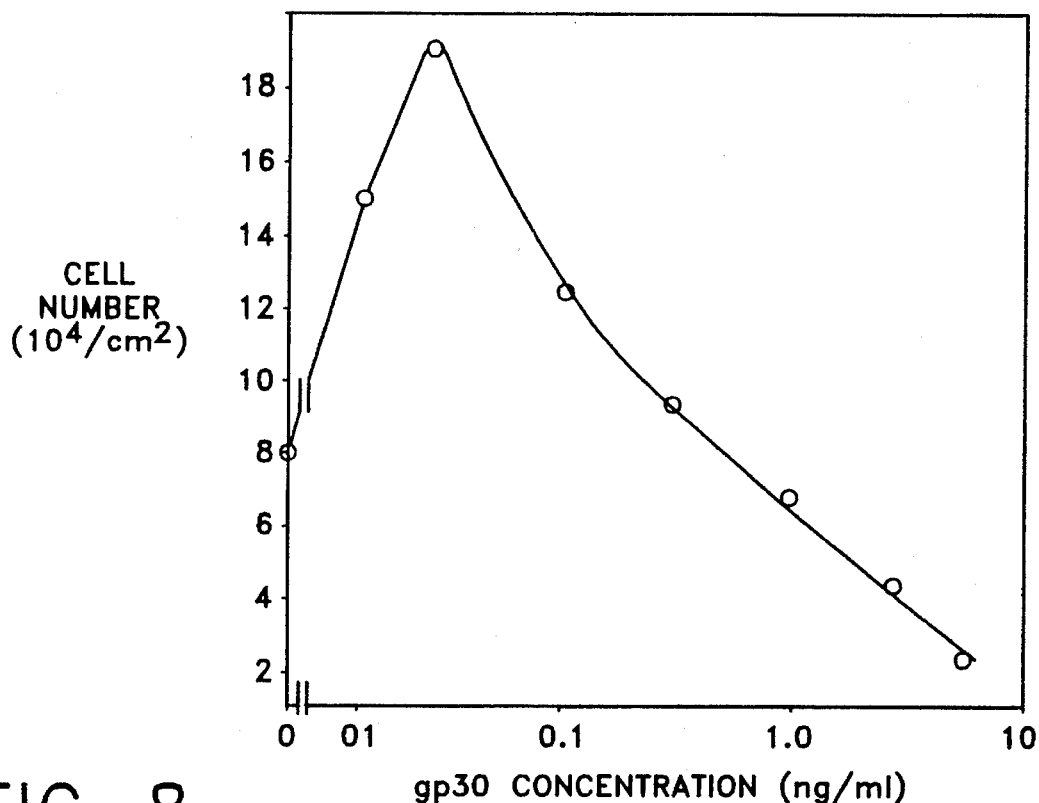
FIG. 7 shows a graph of AU-565 cell numbers per square centimeter after six days of treatment with various concentrations of ligand gp30.

AU-565 cells were also treated with gp30 at concentrations less than 1 ng/ml. Surprisingly, treatment of these cells with a very low dose of gp30, less than 1 ng/ml, resulted in stimulation of cell growth, as can be seen in FIG. 7. This data is shown in Table VI:

TABLE VI

| Cell # 10⁴/cm² | Nuclear area | % Cells lipid | Conc. ng/ml |
|---|---|---|---|
| 8 | 94 | 17 | 0.00 |
| 19.3 | 93 | 14 | 0.03 |
| 12.6 | 101 | 16 | 0.1 |
| 9.6 | 162 | 27 | 0.3 |
| 7.5 | 180 | 46 | 1.0 |
| 4.6 | 206 | 76 | 3.0 |
| 2.3 | 236 | 90 | 6.0 |

Cells not treated with gp30 attained a cell density after six days of approximately 8×10⁴/cm². The results show that maximum growth stimulation occurs at a ligand concentration of about 0.03 ng/mL for gp30, where a cell density of about $1.93 \times 10^5/cm^2$ is attained. Thus, very low concentrations of gp30 appear to agonize malignant cell growth in cells which overexpress HER-2/neu.

With respect to inducing terminal cell differentiation in malignant cells expressing or overexpressing HER-2/neu, more than 90% of AU-565 cells treated with 6 ng/ml-gp30 for 6 days evidenced mature morphology. Treatment of AU-565 cells for 6 days with 6 ng/ml gp30 increased the fraction of cells having identical treatment conditions, the percentage of cells staining positively for casein increased to 90% (control=30%).

Unlike AU-565, MCF-7 cells (which do not express HER-2/neu) treated with 6 ng/ml gp30 did not show marked morphological differences compared to untreated cells.

As with induction of terminal differentiation by monoclonal antibodies specific for the extracellular domain of the HER-2/neu protein, induction of terminal differentiation by gp30 resulted in translocation of HER-2/neu protein from the membrane to the cytoplasm and perinuclear region of the cell.

Figure 8:
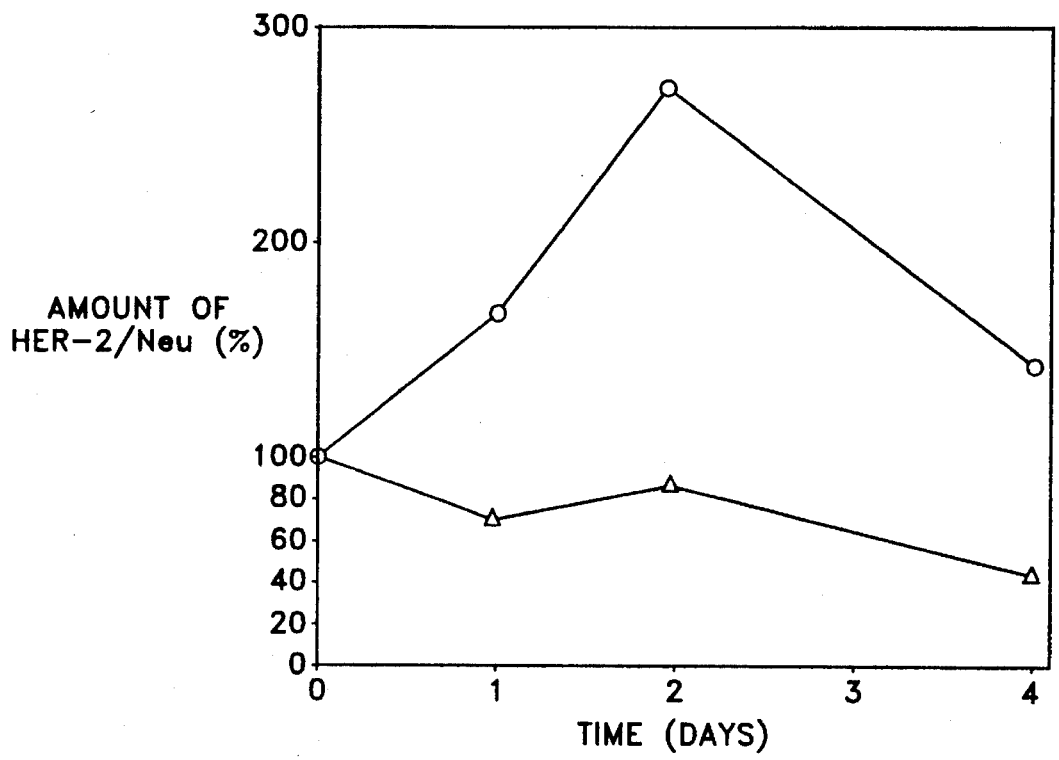
FIG. 8 shows a graph of total cellular HER-2/neu content in AU-565 cells over time as quantified by immunohistochemical stain optical density analysis. Open triangles represent a control sample, while open circles represent a sample treated with 6 ng/mL of gp30 for six days.

During four days in culture, the cell surface of 80–90% of untreated AU-565 cells reacted with the antibody to the HER-2/neu protein, as shown by immunostaining as described in the previous Examples. The remaining cells, which had the morphology of mature cells, showed reduced membrane staining and diffuse cytoplasm staining. Treatment of AU-565 cells with concentrations of gp30 which inhibited growth and induced differentiation markers (over 1 ng/mL) caused a time dependent decrease in membrane staining, and a transient increase in total cellular HER-2/neu staining and cytoplasmic staining, as can be seen in FIG. 8. This diffuse immunostaining increased two- to three- fold during the initial two days of treatment, and decreased in the following two days.

However, treatment of AU-565 cells with 0.03–1 ng/mL gp30 did not change the immunostaining pattern of HER-2/neu, which remained mainly membranous.

The immunostaining for HER-2/neu in MDA-MB 453 cells was less intense, yet the pattern and kinetics of staining, after similar treatment, were similar to those observed in AU-565.

These results indicate that treatment of breast cancer cells with gp30, either inhibited or accelerated breast cancer cell growth, depending on the concentration of the ligand. Ligand concentrations which resulted in cell growth inhibition induced cellular responses that resulted in cell differentiation and acquisition of mature phenotype, which was associated with translocation of of the HER-2/neu protein from the membrane to the perinuclear area.

EXAMPLE VI

Two human breast cancer cell lines, AU-565 and MCF-7, were treated with the chemicals mycophenolic acid (MPA), phorbol 12-myristate 13-Acetate (PMA) or retinoic acid (PA) which are known to induce maturation at low concentrations in a variety of human cell types. The cells were cultured as in Example III. Cells were inoculated into four chamber slides (Nunc) at $0.5 \times 10^4$ or $2 \times 10^5$ cells in 1 mL of medium per chamber or into 100 mm petri dishes at $5 \times 10^4$ cells in 10 mL of medium.

PMA and RA were dissolved in dimethylsulfoxide and stored at $-70°$ C. MPA was dissolved in 150 mM $NaHCO_3$. Treatment with MPA, PMA or RA was initiated 48 hours after cell inoculation. Sparse cultures of the two cell lines were treated for four days with 9 μM MPA, 1.6 nM PMA or 2.5 μM PA.

Three measures of cell differentiation were used. These include cell number, nuclear area ($μm^2$) and precentage of cells expressing lipid droplets. The results are shown in Table VII:

TABLE VII

| Treat. | Cell # $10^4/cm^2$ | Nuclear area | % Cells lipid | Conc. μM |
| --- | --- | --- | --- | --- |
| AU-565 | | | | |
| Control | 6.0 | 80 | 14 | 0.0 |
| MPA | 1.0 | 200 | 63 | 9.0 |
| PKA | 0.8 | 285 | 67 | 1.6 |
| RA | 2.1 | 220 | 97 | 2.5 |
| MCF-7 | | | | |
| Control | 15.0 | 170 | <1 | 0.0 |
| MPA | 2.7 | 163 | 5 | 9.0 |
| PMA | 12.5 | 167 | 6 | 1.6 |
| RA | 7.2 | 166 | 1 | 2.5 |

Cell proliferation was determined by counting cells in a hemocytometer chamber. The cell count was monitored over four days.

Qualitative morphological appearance also characterized differentiation. Analysis of cell morphology in control cultures indicated that 70–80% of untreated, sparsely growing AU-565 cells had the morphology of immature cells, characterized by compact nuclei enclosed by a fine layer of cytoplasm. Another 10–20% displayed a morphology associated with mature cells, having large and lacy nuclei surrounded by sizeable flat cytoplasm Treatment of this cell line with MPA increased the fraction of morphological appearance.

Phenotype expression as a marker of terminal cell differentiation was measured by detecting the production of lipid droplets and casein, both of which are components of human milk. Lipid droplets were detected by a modify "Oil Red O in propylene glycol" method, as described in previous Examples.

The presence of casein was detected by histochemical staining with a human antibody to human casein.

At the time of treatment, about 5% of the cells in the sparse AU-565 cultures and less than 1% of the cells in the MDF-7 cultures contained small lipid droplets. Treatment of AU-565 cultures with MPA or PMA increased the fraction of cells containing the lipid droplets in a time dependent manner to 60–70%. Treatment with RA increased this fraction to more than 90%. Moreover, the lipid droplets in the treated cells were visibly larger than those observed in untreated cells by more than five-fold.

Unlike the AU-565 cells, the MCF-7 cultures treated with MPA, PMA, or RA showed only a small increase in the fraction of cells containing the large lipid droplets: up to about 5% of the cells in cultures treated with MPA or PMA had little or no increase over controls in cultures treated with RA.

Four days after treatment of the two cell lines was begun, the control cultures contained less than 2% of cells that reacted positively with the anti-casein antibody. Treatment of AU-565 cultures with either MPA or RA increased this to 70 to 80%, and treatment with PMA to about 90%. Treatment of the MCF-7 cultures with MPA or RA also increased the percentage of cells staining positively for casein. PMA, even at high doses, had little or no effect on the MCF-7 cell fractions staining positively for this protein.

The HER-2/neu protein was detected by specific antibodies, as described in Example III, and translocation and quantification were performed as also described in Example III.

During four days in culture, the cell surface membrane of 80–90% of untreated AU-565 cells reacted with the two antibodies. The remaining cells, which had the morphology of mature cells, showed reduced membrane staining but increased diffusive cytoplasmic staining. Treatment of AU-565 cells with MPA, PMA or RA caused a time dependent decrease in cell surface membrane concentration of HER-2/neu, and a two to three-fold increase in cytoplasmic concentration of the protein. The immunostaining in the untreated MCF-7 cells was about one-tenth that in untreated AU-565 cells. However the pattern and kinetics of immunostaining after treatment with MPA or RA were similar to those observed for AU-565 cells. PMA, which did not induce differentiation markers in the MCF-7 cells, did not cause a change in the pattern of immunostaining with these antibodies.

EXAMPLE VII

Figure 9A:
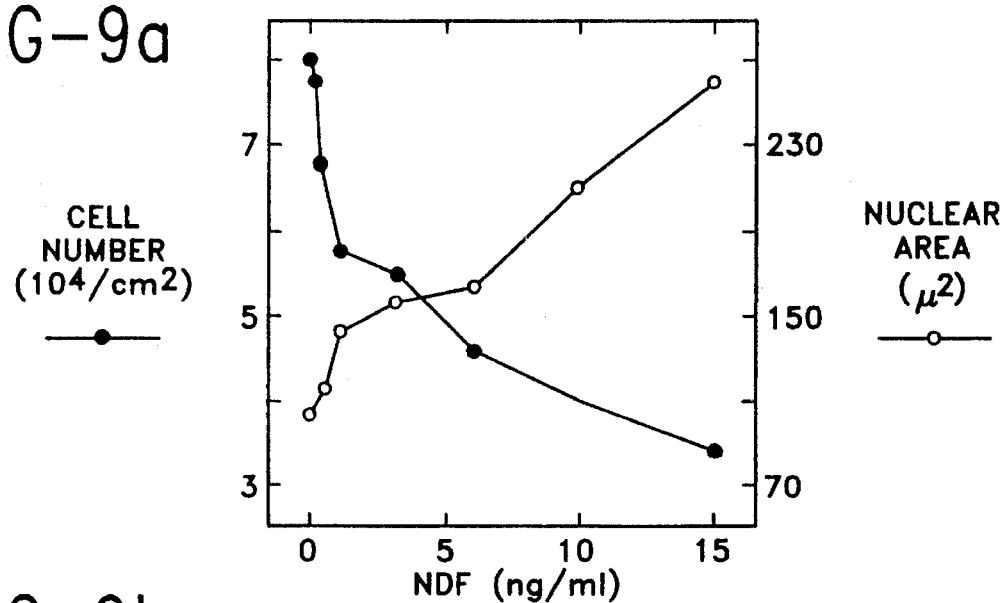
FIGS. 9A and 9B and 9C show the effect of ligand NDF over time on AU-565 cells as measured by cell number and nuclear area (A) and casein an lipid content (B), and on MDA-MB 543 cells as measured by cell number (C).

The biological effects of NDF determined on AU-565 cells in a manner similar to that described above in Example VI for gp30. Briefly, AU-565 cells ($0.4 \times 10^4$) were inoculated into culture dishes in 1 ml of medium supplemented with 10% serum. Twenty-four hours later NDF was added at the indicated concentrations, and the cells were analyzed after four additional days. Cell numbers were determined, and nuclear area was estimated by an imagining system after DNA staining with Feulgen. The numbers given are the calculated averages from ten microscope fields (40× magnification). The results are shown in FIG. 9A.

Figure 9B:
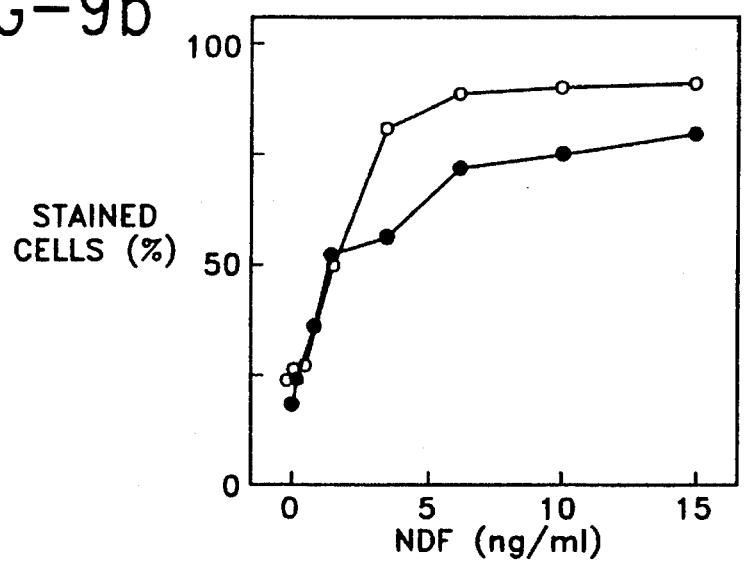

AU-565 cells were treated as above and then stained for casein and lipids as described above. The average fractions of cells stained positively for lipids (closed circles) and casein (open circles) were determined by counting stained cells in ten microscope fields (40× magnification). The variation among fields did not exceed 15%. The results are shown in FIG. 9B.

Figure 9C:
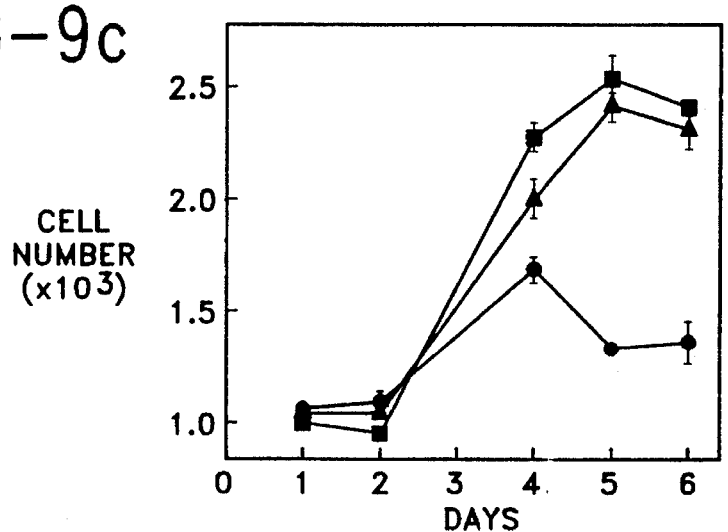

MDS-MB 543 ($10^5$) cells were inoculated into multiwell culture dishes and after 24 hours their medium was replaced with serum-free medium. This was supplemented with 5 ng/ml EGF (squares) of 5 ng/ml NDF (circles). Control cultures (triangles) received no growth factor. The dishes were then incubated at 37° C., and on the indicated days cell numbers were determined in duplicate cultures. The averages and their ranges (vertical bars) are shown in FIG. 9C.

EXAMPLE VIII

In addition to the expression of HER-2/neu protein in cancer cells, The expression of ICAM-1 also correlates with induced differentiation upon treatment. Briefly, AU-565 cells were treated with NDF, N29 or N28 at a concentration of 10 μg/mL in a manner similar to that described in Example III. A monoclonal antibody against ICAM-1 (Becton Dickinson Immunocytometry Systems, San Jose, Calif.) was applied to treated cells. Expression of ICAM-1, HER-2/neu, cell number, percent of cells stained for lipid droplets and nuclear area ($\mu m^2$) were determined by methods described in Example III. Units for ICAM-1 and HER-2/neu expression are arbitrary with "1" representing the value of expresion in control cells as measured by image cytometry. The results are shown in Table VIII.

TABLE VIII

| Treat. | Cell # $10^4/cm^2$ | Nuclear area | % Cells lipid | ICAM | HER-2/neu |
|---|---|---|---|---|---|
| CONTROL | 6 | 73.3 | 13 | 1 | 1 |
| NDF | 3.5 | 187 | 73 | 3.3 | 1.3 |
| N29 | 3.1 | 156 | 66 | 1.7 | 1.4 |
| N28 | 7.05 | 85 | 15 | 1.2 | 1.2 |

Thus, the methods of the present invention provide a powerful prognostic tool for predicting the effectiveness of a cancer therapy using monoclonal antibodies or ligands which induce differentiation of cancer cells. The methods of the present invention also provide for the screening of putative anti-cancer agents for the determination of efficacy of the agent in treatment of a malignancy. Monoclonal antibodies and ligands identified in accordance with the present invention induce the expression of mature phenotype and terminal cell differentiation, thereby inhibiting the growth of a malignancy. Additionally, the methods of the invention provide for the determination of beneficial does of, and/or improved combinations of, such therapeutic agents. Finally, the methods of the present invention are easily performed, and are therefore time andnd cost-effective, as well as minimally traumatic to a cancer patient.

While the invention has been described with some specificity, modifications apparent to those with ordinary skill in the art may be made without departing from the scope of the invention.

---

I claim:

1. A method for determining, in vitro, the effectiveness of a therapeutic agent for treatment of a cancer, said agent comprising at least one compound having specific binding affinity for an oncogene product, wherein malignant cells of the cancer express or overexpress the oncogene product, the method comprising the steps of:

(a) obtaining viable malignant cells which express or overexpress at least one oncogene product and dividing the same into at least first and second portions;

(b) treating the first portion comprising viable malignant cells with a sufficient quantity of said agent comprising at least one compound having specific binding affinity for an oncogene product and contacting the second portion with a composition which is devoid of the compound or compounds having specific binding affinity for the oncogene product;

(c) incubating the first and second portions in a physiologically acceptable medium for an amount of time sufficient to induce a percentage of the viable malignant cells of said first portion to terminally differentiate; and (d) comparing the percentage of cells in the first portion which exhibit evidence of said terminal differentiation to the percentage of cells in the second portion which exhibit morphological evidence of terminal differentiation.

2. The method of claim 1 wherein the viable malignant cells are obtained from a patient.

3. The method of claim 1 wherein the oncogene product is expressed on the surface of cells and the agent has a binding affinity for the extracellular domain of the oncogene product.

4. The method of claim 3 wherein the oncogene product is HER-2/neu protein.

5. The method of claim 4 wherein the compound comprises at least one monoclonal antibody.

6. The method of claim 4 wherein the compound comprises at least one ligand.

7. The method of claim 1 wherein evidence of terminal differentiation is measured by translocation of the HER-2/neu protein from the surface of a cell to the cytoplasm of the cell.

8. The method of claim 1 wherein evidence of terminal differentiation is measured by an increased expression of one or more cell adhesion molecules.

9. The method of claim 7 wherein translocation is determined immunohistochemically with one or more labeled antibodies for the HER-2/neu protein.

10. The method of claim 1 wherein morphological evidence of terminal differentiation is measured by an increase in total nuclear area.

11. The method of claim 8 wherein the cell adhesion molecule is ICAM-1.

12. The method of claim 1 wherein morphological evidence of terminal differentiation is measured by one or more changes selected from the group consisting of (a) translocation of HER-2/neu protein from the surface of a cell to the cytoplasm of the cell, (b) an increased expression of one or more cell adhesion molecules, and (c) an increase in total nuclear area.

13. The method of claim 1 wherein the cancer is breast cancer and terminal differentiation is measured by production of one or more milk components.

14. The method of claim 13 wherein the milk component is lipid droplets.

15. A method for determining, in vitro, the effectiveness of a therapeutic agent for treatment of a cancer, said agent comprising at least one compound having specific binding affinity for HER-2/neu product, wherein malignant cells of the cancer express or overexpress HER-2/neu product, the method comprising the steps of:

(a) obtaining viable malignant cells from a breast, stomach, ovarian or salivary tissue biopsy and dividing the same into at least first and second portions;

(b) treating the first portion comprising viable malignant cells with a sufficient quantity of said agent comprising at least one compound having specific binding affinity for HER-2/neu product and contacting the second portion with a composition which is devoid of the compound or compounds having specific binding affinity for HER-2/neu product;

(c) incubating the first and second portions in a physiologically acceptable medium for an amount of time sufficient to induce a percentage of the viable malignant cells of said first portion to terminally differentiate; and (d) comparing the percentage of cells in the first portion which exhibit translocation of HER-2/neu product to the percentage of cells in the second portion which exhibit translocation of HER-2/neu product.

16. The method of claim 5 or 15 wherein the compound is selected from the group consisting of monoclonal antibodies produced by the hybridomas deposited as I-1260, I-1261, I-1262 and I-1263.

17. The method of claim 6 or 15 wherein the compound is selected from the group consisting of gp30 and neu differentiation factor.

* * * * *